United States Patent
Coelho et al.

(10) Patent No.: US 11,141,435 B2
(45) Date of Patent: Oct. 12, 2021

(54) BUOYANCY-ACTIVATED CELL SORTING (BACS)-COMPATIBLE ACTIVATION/TRANSDUCTION SYSTEMS AND METHODS

(71) Applicant: ThermoGenesis Corporation, Rancho Cordova, CA (US)

(72) Inventors: Philip H. Coelho, Rancho Cordova, CA (US); William Busa, Rancho Cordova, CA (US); Jonathan Ellis, Rancho Cordova, CA (US); Dalip Sethi, Rancho Cordova, CA (US)

(73) Assignee: ThermoGenesis Corporation, Rancho Cordova, CA (US)

(*) Notice: Subject to any disclaimer, the term of this patent is extended or adjusted under 35 U.S.C. 154(b) by 0 days.

(21) Appl. No.: 16/353,071

(22) Filed: Mar. 14, 2019

(65) Prior Publication Data

US 2019/0282619 A1 Sep. 19, 2019

Related U.S. Application Data

(60) Provisional application No. 62/643,081, filed on Mar. 14, 2018.

(51) Int. Cl.
| | |
|---|---|
| *C12N 5/0783* | (2010.01) |
| *A61K 48/00* | (2006.01) |
| *A61K 35/17* | (2015.01) |
| *A61K 47/65* | (2017.01) |
| *A61K 47/69* | (2017.01) |
| *C07K 16/18* | (2006.01) |
| *A61K 9/127* | (2006.01) |
| *C07K 14/725* | (2006.01) |

(52) U.S. Cl.
CPC ............ *A61K 35/17* (2013.01); *A61K 9/1277* (2013.01); *A61K 47/65* (2017.08); *A61K 47/6911* (2017.08); *C07K 14/7051* (2013.01); *C07K 16/18* (2013.01)

(58) Field of Classification Search
None
See application file for complete search history.

(56) References Cited

U.S. PATENT DOCUMENTS

| | | | | |
|---|---|---|---|---|
| 6,806,045 B2 * | 10/2004 | Kulseth | ............... | C12N 15/1034 435/325 |
| 7,807,377 B2 | 10/2010 | Albani | | |
| 9,695,394 B1 | 7/2017 | Coelho et al. | | |
| 9,770,411 B2 | 9/2017 | Bioley et al. | | |
| 9,821,111 B2 | 11/2017 | Coelho et al. | | |
| 2015/0219636 A1 * | 8/2015 | Rychak | ............... | G01N 33/5432 435/5 |
| 2017/0176305 A1 | 6/2017 | Shi et al. | | |
| 2017/0348401 A1 | 12/2017 | Bioley et al. | | |
| 2018/0171295 A1 * | 6/2018 | Shi | ....................... | C12N 5/0087 |

FOREIGN PATENT DOCUMENTS

| | | | |
|---|---|---|---|
| WO | WO 15/162211 | * | 10/2015 |
| WO | 2015/175344 A1 | | 11/2015 |

OTHER PUBLICATIONS

Tumaini et al., Cytotherapy, 2013, 15: 1406-1415.*
Miltenyi Data Sheet, 2020.*
Mock et al., Cytotherapy, 2016, 18: 1002-1011.*
Bioley et al. (2012). The phagocytosis of gas-filled microbubbles by human and murine antigen-presenting cells. Biomaterials 33:333-342. doi:10.1016/j.biomaterials.2011.09.045.
Bioley et al. (2012). Gas-filled microbubble-mediated delivery of antigen and the induction of immune responses. Biomaterials 33:5935-5946. doi:10.1016/j.biomaterials.2012.05.004.
Sasaki and K Okuda (2000). The use of conventional immunologic adjuvants in DNA vaccine preparations In: DNA Vaccines: Methods and Protocols (D.B. Lowrie and R.G. Whalen, eds., Humana Press).
Prakken et al. (2000). Artificial antigen-presenting cells as a tool to exploit the immune 'synapse.' Nature Medicine 6(12):1406-1410.
Koffeman et al. (2007). Identification and manipulation of antigen specific T-cells with artificial antigen presenting cells. Methods Mol Med 136:69-86.
Zappasodi et al. (2008). The effect of artificial antigen-presenting cells with preclustered anti-CD28/-CD3/-LFA1 monoclonal antibodies on the induction of ex vivo expansion of functional human antitumor T cells. Haematologica 93:1523-1534.
Haveman et al. (2013). Selection of perforin expressing CD4+ adenovirus-specific T-cells with artificial antigen presenting cells. Clinical Immunology 146:228-239.
http://www.miltenyibiotec.com/en/clinical-applications/clinimacs-system/clinimacs-instruments/clinimacs-prodigy/clinimacs-prodigy-instruments.aspx, printed May 2019.

(Continued)

*Primary Examiner* — Ileana Popa
(74) *Attorney, Agent, or Firm* — McDonnell Boehnen Hulbert & Berghoff LLP

(57) ABSTRACT

Disclosed herein are methods for contacting in a closed container a host liquid including target cells, microbubble reagents comprising gas-core lipid-shelled microbubbles, and one or more antibodies or other ligands that bind to cell surface molecules on the target cells, wherein the one or more antibodies or other ligands are bound to the target cells or the microbubbles, wherein the contacting under conditions to produce target cells linked to microbubbles via the one or more antibodies or other ligands and activating the target cells to generate activated target cells.

24 Claims, 11 Drawing Sheets

(56) References Cited

OTHER PUBLICATIONS

Trickett and Y.L. Kwan (2003). T cell stimulation and expansion using anti-CD3/CD28 beads. J. Immunol. Methods 275(1-2):251-255. https://doi.org/10.1016/S0022-1759(03)00010-3.
Frecha, C Levy, F.-L. Cosset, E Verhoeyen (2010). Molecular Therapy 18(10):1748-1757. DOI: http://dx.doi.org/10.1038/mt.2010.178.
https://assets.thermofisher.com/TFS-Assets/LSG/manuals/MAN0008945_dynabeads_CD3CD28CTS.pdf, Jul. 2017.
http://www.miltenyibiotec.com/en/products-and-services/macs-cell-culture-and-stimulation/stimulation-reagents/polyclonal-stimulation/t-cell-activation-expansion-kit-human.aspx#tabs-productpage-3, Printed May 2019.

\* cited by examiner

| ACTIVATION METHOD | POST-ACTIVATION | | POST-TRANSDUCTION | |
|---|---|---|---|---|
| | CD69+ | CD25+ | CD69+ | CD25+ |
| CD3/28 microbubbles | 80% | 79% | 29% | 93% |
| CD3/28 Dynabeads | 80% | 80% | 19% | 88% |

FIG. 11

BUOYANCY-ACTIVATED CELL SORTING (BACS)-COMPATIBLE ACTIVATION/TRANSDUCTION SYSTEMS AND METHODS

CROSS REFERENCE

This application claims priority to U.S. Provisional Patent Application Ser. No. 62/643,081 filed Mar. 14, 2018, incorporated by reference herein in its entirety.

BACKGROUND OF THE DISCLOSURE

Genetic modification of human lymphocytes is an increasingly important step in the development and manufacturing of therapeutic live cell-based therapies such as chimeric antigen receptor T (CAR-T) cells. CAR-T cells, such as the first-of-its-kind FDA-approved KYMRIAH (tisagenlecleucel) for acute lymphoblastic leukemia, are a patient's own (autologous) T lymphocytes manufactured into cancer-killing cells in what is today a complex, costly and time-consuming laboratory process.

Today, the CAR-T manufacturing process typically involves the sequential steps of (i) leukapheresis of the patient's blood to concentrate a large number of autologous white blood cells, which leukapheresis product' is then shipped from the clinic to a manufacturing laboratory site; (ii) a preliminary cell fractionation of the leukapheresis product to prepare a more nearly pure suspension of mononuclear cells (MCs) with reduced numbers of contaminating non-MC cells (typically achieved via density gradient centrifugation using Ficoll™ or a similar soluble polymer as a density agent), yielding a so-called peripheral blood mononuclear cell preparation (PBMCs); (iii) a further round of purification to isolate from the PBMCs a more nearly pure population of $CD3^+$ T lymphocytes (the specific cell type that is the starting material for CAR-T manufacturing), today typically achieved via magnetic-activated cell sorting (MACS) using magnetic nanoparticles conjugated with anti-CD3 antibodies; followed by (iv) 'activation' of the isolated $CD3^+$ cells to render them susceptible to integration of foreign DNA into their chromosomes (activation typically being accomplished by exposing the cells to microbeads conjugated with anti-CD3/anti-CD28 antibodies for about 1 to 3 days in culture); followed by (v) a process termed 'transduction,' in which the activated $CD3^+$ cells are contacted with a genetically engineered adenovirus vector containing an artificial gene construct encoding a chimeric (two-part) transmembrane fusion protein comprising an extracellular anti-CD19 single chain antibody fragment and intracellular T cell signaling (CD3-ζ) and co-stimulatory (4-1BB) domains (the so-called chimeric antigen receptor, or CAR). Finally, the patient's transduced, CAR-expressing T cells (CAR-T cells) are expanded (allowed to reproduce) in culture to yield a therapeutic dose of CAR-T cells ($0.2 \times 10^6$ to $2.5 \times 10^8$ viable CAR-expressing T cells in the case of tisagenlecleucel) for intravenous infusion back into the patient following lymphodepleting chemotherapy.

The KYMRIAH manufacturing process outlined here is largely similar to that of today's only other FDA-approved CAR-T cell therapeutic, Yescarta (axicabtagene ciloleucel, for diffuse large B-cell lymphoma), as it also is to those of an increasingly large number of other genetically modified lymphocyte therapeutic candidates currently in preclinical development or clinical trials around the world. From a commercialization perspective, a distinguishing characteristic of these manufacturing processes is their complex, labor-intensive, and inefficient nature, contributing to these life-saving therapeutics' extremely high cost ($373,000 or $475,000 for a single-dose course of treatment with Yescarta or KYMRIAH, respectively). As practiced today, this manufacturing paradigm typically involves dozens of sequential liquid handling steps and transfers of the in-process material to new containers (with associated cell losses) and relatively inefficient (low target cell recovery) cell isolation and cell washing steps imposing additional cell losses, which must in turn be compensated for by additional time devoted to cell expansion (consuming costly cell culture media and imposing additional liquid-handling steps, as well as negatively impacting the potential proliferative capacity of the cells in vivo) in order to achieve a therapeutic dose. Such compounded manufacturing inefficiencies and lengthy manufacturing time courses negatively impact not only the cost of goods, but, more importantly, also the critically ill patient's prognosis, as they impact the probability that an effective therapeutic dose can be manufactured in a timely manner, if at all.

SUMMARY

In a first aspect are disclosed methods, comprising contacting in a closed container a host liquid comprising target cells, microbubble reagents comprising gas-core lipid-shelled microbubbles, and one or more antibodies or other ligands that bind to cell surface molecules on the target cells, wherein the one or more antibodies or other ligands are bound to the target cells or the microbubbles, wherein the contacting occurs for a time and under conditions sufficient to produce target cells linked to microbubbles via the one or more antibodies or other ligands; and activating the target cells to generate activated target cells.

In one embodiment, the method further comprises concentrating the target cells linked to microbubbles in the closed container. In another embodiment, the method of further comprises collapsing and/or disrupting the microbubbles after producing the target cells linked to microbubbles. In a further embodiment, the collapsing and/or disrupting the microbubbles occurs after concentrating the target cells linked to microbubbles in the closed container. In various embodiments, the collapsing and/or disrupting the microbubbles occurs within about 180 minutes after initiating the contacting, between about 1 minute and about 180 minutes after initiating the contacting, between about 2 minutes and about 60 minutes after initiating the contacting, and/or between about 5 minutes and about 30 minutes after initiating the contacting. In another embodiment, the activating is achieved without separating the target cells from the microbubbles or microbubble residua.

In one embodiment, the contacting comprises contacting in the closed container the host liquid comprising (i) target cells bound to the one or more antibodies or other ligands, and (ii) microbubbles capable of binding to the one or more antibodies or other ligands directly or indirectly via a linker. In another embodiment, the contacting comprises contacting in the closed container the host liquid comprising (i) target cells, and (ii) microbubble reagents displaying one or more antibodies or other ligands that bind to cell surface molecules on the target cells. In a further embodiment, the one or more antibodies or other ligands comprise one or more antibodies.

In one embodiment, the method further comprises transducing the activated target cells with a vector, such as a viral vector, comprising a transgene to produce transduced target cells, wherein the transducing comprises contacting the activated target cells with gene transduction reagents comprising a vector comprising a transgene under conditions suitable to transduce the activated target cells. In another embodiment, the transducing is carried out in the closed container. In a further embodiment, the transducing comprises activated CD3$^+$ target cells being contacted with a genetically engineered viral vector comprising an artificial gene construct encoding a chimeric (two-part) transmembrane fusion protein comprising an extracellular anti-CD19 single chain antibody fragment and intracellular T cell signaling (CD3-ζ) and co-stimulatory (4-1BB) domains (the so-called chimeric antigen receptor, or CAR), and wherein the resulting transduced target cells are CAR-T cells. In another embodiment, the interval between initiating the contacting and initiating the transducing by contacting the activated CD3$^+$ target cells with the genetically engineered viral vector is between about 12 hours and about 36 hours.

In one embodiment the method further comprises expanding the activated target cells or the transduced target cells, wherein the expanding comprises culturing the activated target cells or the transduced target cells under conditions suitable to promote proliferation of the activated target cells or the transduced target cells. In another embodiment, the expanding is carried out in the closed container.

In one embodiment, the target cells comprise CD3+ T cells, and wherein the one or more antibodies comprise anti-CD3 and anti-CD28 antibodies. In another embodiment, the host liquid comprises blood, leukapheresis product, or diluted or otherwise processed versions thereof. In a further embodiment, the host liquid comprises a peripheral blood mononuclear cell (PBMC) preparation.

In one embodiment, the method further comprises harvesting the expanded activated target cells or transduced target cells to produce a harvested activated cell population or a harvested transduced cell population; wherein the harvesting is optionally carried out in the closed container. In another embodiment, the method further comprises washing the harvested activated cell population or the harvested transduced cell population; wherein the washing is optionally carried out in the closed container. In a further embodiment, the methods further comprise transferring the harvested activated cell population or the harvested transduced cell population to a medium suitable for infusion, or transferring the harvested activated cell population or the harvested transduced cell population to a cryopreservation medium; wherein the transferring is optionally carried out in the closed container. In another embodiment, the host liquid is partially depleted of non-target cells prior to the activating step.

In one embodiment, the functionally closed container comprises:
 (a) a cartridge comprising
  (i) a processing container comprising at least one input port, a first exit port, and a second exit port;
  (ii) a second container comprising an input port;
  (iii) a third container comprising an input port and a first exit port;
  (iv) a first conduit connecting the first exit port of the processing container and the input port of the second container, wherein the first conduit comprises a first reversible closing device, wherein the second container is transiently fluidically connected to the processing container such that fluid flow only from the processing container to the second container may occur when the first reversible closing device is opened;
  (v) a second conduit connecting the second exit port of the processing container and the input port of the third container, wherein the second conduit comprises a second reversible closing device, wherein the third container is transiently fluidically connected to the processing container such that fluid flow only from the processing container to the third container may occur when the second reversible closing device is opened;
 (b) a transfer container comprising at least one port;
 (c) an at least third conduit connecting
  (i) the first exit port of the third container to the at least one port of the transfer container, and
  (ii) the at least one port of the transfer container to the at least one input port of the processing container;
  wherein the at least third conduit comprises at least a third reversible closing device, such that (A) the third container is transiently fluidically connected to the transfer container, and (B) the transfer container is transiently fluidically connected to the processing container; wherein the at least third conduit is configured such that only one of the following may be true
   (I) fluid flow only from the third container to the transfer container may occur when the at least third reversible closing device is opened; or
   (II) fluid flow only from the transfer container to the processing container may occur when the at least third reversible closing device is opened; and
 (d) a control module configured to control activity in at least the cartridge, and the first and second conduits.

In one embodiment, the transfer container is internal to the cartridge. In another embodiment, the at least third conduit comprises a single conduit. In a further embodiment, the at least third conduit comprises T or Y connector disposed between the third container and transfer container and between the transfer container and the processing container. In another embodiment, the at least one port of the transfer container comprises a first input port and an exit port.

In one embodiment, the at least third conduit comprises:
 (i) a third conduit connecting the exit port of the third container to the input port of the transfer container, wherein the third conduit comprises a third reversible closing device, such that the third container is transiently fluidically connected to the transfer container such that fluid flow only from the third container to the transfer container may occur when the third reversible closing device is opened; and
 (ii) a fourth conduit connecting the exit port of the transfer container to the at least one input port of the processing container, wherein the fourth conduit comprises a fourth reversible closing device, such that the transfer container is transiently fluidically connected to the processing container, such that fluid flow only from the transfer container to the processing container may occur when the fourth reversible closing device is opened.

In another embodiment, the at least one input port of the processing container comprises a first input port and a second input port, wherein the at least third conduit, or the fourth conduit (when present), connects the exit port of the transfer container to the first input port of the processing container. In a further embodiment, a first medium input conduit connects the second input port of the processing container to at least one medium reservoir, wherein the first medium input conduit comprises at least a fifth reversible closing device, wherein the at least one medium reservoir is transiently fluidically connected to the processing container such that fluid flow only from the at least one medium reservoir to the processing container may occur when the at least fifth reversible closing device is opened. In another embodiment, the at least one port of the transfer container further comprises a second input port. In a further embodiment, a second medium input conduit connects the second input port of the transfer container to at least one medium reservoir, wherein the second medium input conduit comprises at least a sixth reversible closing device, wherein the at least one medium reservoir is transiently fluidically connected to the processing container such that fluid flow only from the at least one medium reservoir to the transfer container may occur when the at least sixth reversible closing device is opened.

In another embodiment, the cell separation system further comprises a mixer. In various embodiments, the mixer may comprises a static mixer, the mixer may comprise an impeller disposed on an internal surface of a roof of the cartridge, the mixer may comprise an impeller spaced away from an internal surface of a roof of the cartridge, the mixer may comprise a peristaltic pump comprising a pump conduit having a first end and a second end, wherein the first end of the pump conduit is positioned in the processing chamber, and wherein the second end of the pump conduit is positioned outside of the processing chamber and is connected to the at least one input port of the processing chamber; the mixer may comprise a mixing module comprising a bottom portion and a top portion, wherein the cartridge is configured to be positioned in the bottom portion, and wherein the top portion is configured to be removably coupled to the bottom portion; the mixing module may include a rotatable component coupled to the bottom portion, and wherein the rotatable component is configured to rotate the cartridge on its vertical axis by 180 degrees or by 360 degrees; and/or the mixing module may be configured to increase a temperature of the cartridge when the cartridge is positioned in the bottom portion of the mixing module.

In one embodiment, the first medium input conduit and/or the second medium input conduit further comprise a filter. In another embodiment, the second container comprises an exit port coupled to a first waste conduit. In a further embodiment, the processing container further comprises a sterile vent coupled to a second waste conduit.

In one embodiment, the transduced cells are CAR-T cells. In another embodiment, the methods further comprise administering to a subject in need thereof an amount of the harvested activated cell population or the harvested transduced cell population effective to treat a disorder in the subject.

In another aspect are disclosed isolated cell suspensions, comprising a harvested activated cell population or a harvested transduced cell population produced by the methods of any embodiment or combination of embodiments disclosed herein. In one embodiment, the isolated cell suspension comprises CAR-T cells.

In a further aspect are provided methods for treating a subject in need thereof, comprising administering to the subject an amount of the harvested activated cell population or a harvested transduced cell population disclosed herein effective to treat a disorder in the subject. In one embodiment, the subject has cancer.

In another aspect are disclosed kits, comprising any combination of:
(a) microbubbles for the activation and transduction of a target cell type, wherein the kit provides either:
(i) manufactured reagents, wherein the microbubbles and antibodies are provided already attached to each other, optionally via intermediate linkers, or
(ii) separately packaged microbubbles and antibodies with complementary linkers, which spontaneously assemble into antibody bound microbubbles when added to the host liquid;
(b) one or more cartridges of the type disclosed in the '394 patent;
(c) buffers suitable for use with the provided reagents and cartridges to activate and transduce the target cells;
(d) buffers suitable for viral transduction of the activated target cells within the provided cartridges; and
(e) viral vectors suitable for transduction of the activated target cells within the provided cartridges.

DESCRIPTION OF THE FIGURES

FIG. 11: CD3+ T cell expression of the activation markers CD69 and CD25 following activation and transduction, for cells activated with either CD3/CD28 BACS microbubbles or CD3/CD28 Dynabeads™.

DETAILED DESCRIPTION

Figure 1:
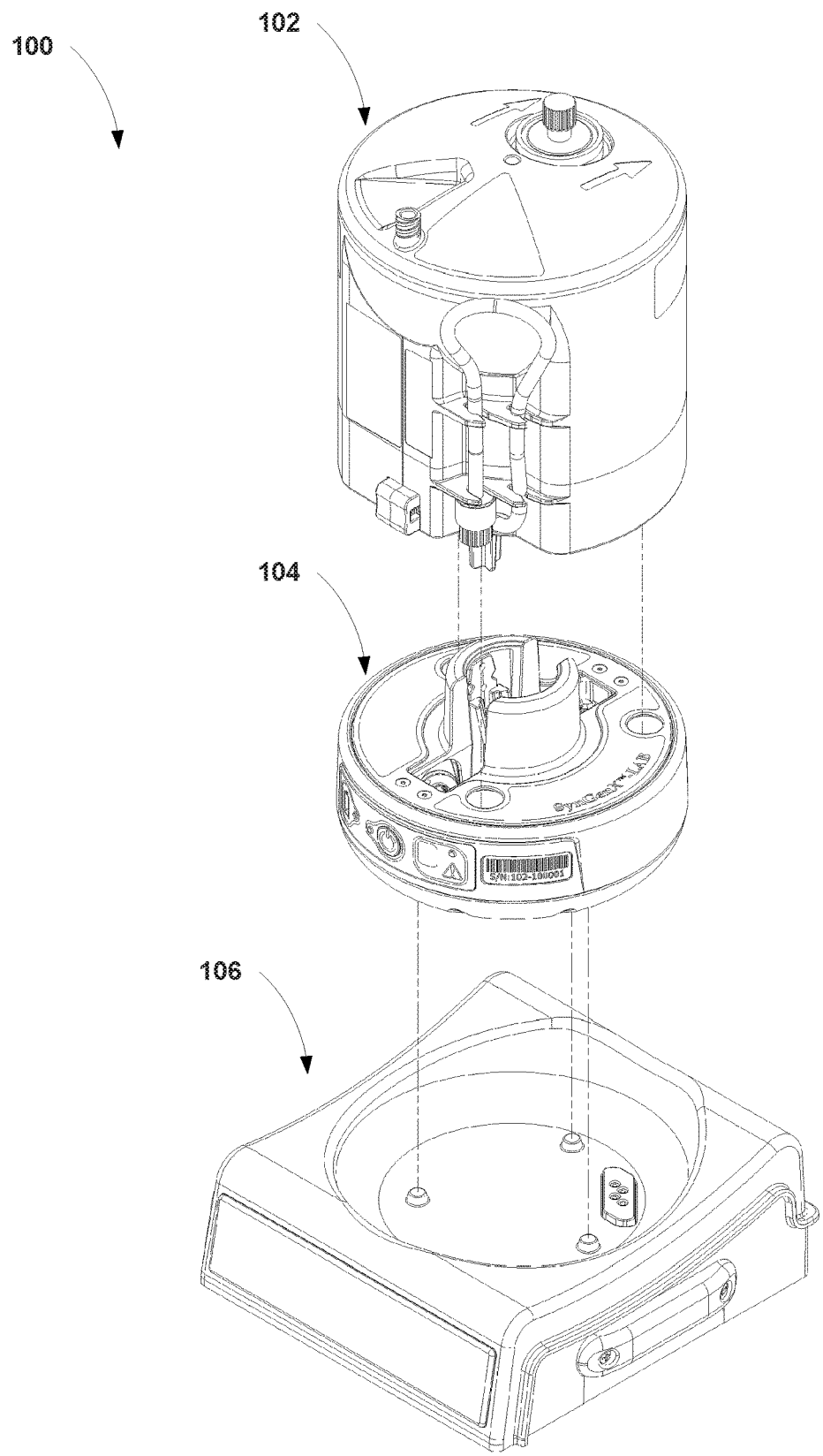
FIG. 1 is an exploded view of a closed system, according to an example embodiment.

As used herein, the singular forms "a", "an" and "the" include plural referents unless the context clearly dictates otherwise. "And" as used herein is interchangeably used with "or" unless expressly stated otherwise.

As used herein, the term "about" means+/−5% of the recited parameter.

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In one aspect methods are provided, comprising contacting in a closed container a host liquid comprising target cells, microbubble reagents comprising gas-core lipid-shelled microbubbles, and one or more antibodies or other ligands that bind to cell surface molecules on the target cells, wherein the one or more antibodies or other ligands are bound to the target cells or the microbubbles, wherein the contacting occurs for a time and under conditions sufficient to produce target cells linked to microbubbles via the one or more antibodies or other ligands; and activating the target cells to generate activated target cells.

The methods of the disclosure proceed from the two interrelated surprising discoveries that (i) the buoyancy-activated cell sorting (BACS) microbubble reagents of the systems and methods of U.S. Pat. No. 9,821,111 (hereinafter the '111 patent) can be formulated in a composition that achieves both the highly efficient target cell recovery and purity previously documented in the '111 patent while also, in the same single contacting of the target cells with those BACS reagents, achieving the highly efficient activation of the target lymphocytes that is an established prerequisite for their efficient transduction; and (ii) that these BACS-isolated and -activated target cells (including but not limited to $CD3^+$ T cells) can subsequently be efficiently transduced with a transgene-bearing vector (including but not limited to a retroviral vector), thus enabling a dramatically simplified 'one pot' manufacturing process for transgenic target cells (such as lymphocytes), from the starting product (such as leukapheresis product or peripheral blood) to transgene-expressing target cells, with high overall efficiency (target cell recovery and transduction) at low capital cost.

The present disclosure provides combined BACS/cell-activation reagents, systems and methods that can be compatible with a one-pot workflow from pre-processing of blood or leukapheresis product through viral transduction of T cells, that avoid the use of solid beads and the resulting need for removal of the beads from the manufactured cells prior to clinical use, and that are compatible with buoyancy-activated cell sorting methods and reagents, while maintaining viability and manufacturing suitability of the cells in a functionally closed aseptic container. The practice of these methods on volumes of starting materials exemplified by blood, bone marrow, or leukapheresis product containing clinically or commercially relevant numbers of stem, progenitor, immune or other cells can provide compositions of target cells that are significantly higher in recovery, purity, and extent of activation and subsequent transduction than can be consistently obtained by other known methods. Additionally, the disclosure simplifies the CAR-T manufacturing workflow by extending the number of manufacturing steps that may be performed in a 'one-pot' process (employing, for example, the cartridge of the '394 patent) from initial pre-processing of blood or leukapheresis product through to T cell activation and transduction, thus offering the potential for improved workflow efficiency and reduced manufacturing cost.

As used herein, a "target cell" (plural, "target cells") is the cell or cells to be activated and transduced in the methods of this disclosure. The methods and systems of the disclosure may be used with any suitable target cell to be activated and transduced, including but not limited to T cells (including but not limited to CD3+, CD4+, and Treg cells).

In one specific embodiment, the target cells comprise CD3+ T cells, and the one or more antibodies comprise anti-CD3 and anti-CD28 antibodies, or the one or more ligands comprise CD3 and CD28 binding ligands. In a further embodiment, the CD3+ cells may be quiescent naïve T cells. In another embodiment, the contacting may comprise contacting in the presence of interleukin-2 (IL-2) for some portion of the contacting period (i.e.: Il-2 is not required for binding of the antibodies to the target cells, but may be used to promote activation). In one embodiment, the host liquid containing the CD3+ cells may be blood, leukapheresis product, or diluted or otherwise processed versions thereof. In another embodiment, the host liquid may comprise a peripheral blood mononuclear cell (PBMC) preparation.

As used herein, a "closed system" is a process system with equipment designed and operated such that the product is not exposed to the room environment. Materials may be introduced to a closed system, but the addition must be done in such a way to avoid exposure of the product to the room environment (e.g., by 0.2 μm pore size filtration).

The contacting comprises contacting a host liquid comprising target cells, with microbubble reagents comprising gas-core lipid-shelled microbubbles, and one or more antibodies or other ligands that bind to cell surface molecules on the target cells, wherein the one or more antibodies or other ligands are bound to the target cells or the microbubbles. Thus, in one embodiment the contacting comprises contacting in the closed container the host liquid comprising (i) target cells bound to the one or more antibodies or other ligands, and (ii) microbubbles capable of binding to the one or more antibodies or other ligands directly or indirectly via a linker. In another embodiment, the contacting comprises contacting in the closed container the host liquid comprising (i) target cells, and (ii) microbubble reagents displaying one or more antibodies or other ligands that bind to cell surface molecules on the target cells. In one embodiment, the one or more antibodies or other ligands comprise one or more antibodies.

The contacting occurs for a time and under conditions sufficient to produce target cells linked to microbubbles via the one or more antibodies or other ligands. Any suitable conditions for promoting binding of target cells to the one or more microbubble-bound-antibodies or the one or more microbubble-bound ligands to generate microbubble-bound target cells, or for promoting binding of microbubbles to the one or more target cell-bound antibodies or the one or more target cell-bound ligands to generate the microbubble-bound target cells may be used, such as those disclosed herein and in the '111 patent. It is well within the level of those of skill in the art to determine suitable conditions based on the teachings herein. In one embodiment, the contacting comprises a single contacting of the target cells with the microbubbles (i.e.: no additional microbubbles are added to the host liquid after the initial contacting step). This embodiment is a significant improvement over current methods using DYNABEADS®, which in some cases must be replenished during activation.

As used herein, the term "activating: or "activation" means the initiation and development of a previously quiescent cellular process or sequence of processes whose activity is/are required in order to meet a particular technical, medical, or business goal. By way of examples, without limitation:

(a) In the particular case of genetically engineered naive T cells "activation" means the triggering and development of a sequence of cell biological and biochemical processes that render 20% or more of the cells transduction-competent (i.e., able to be sufficiently efficiently transduced with and to express a transgene), where these processes may include, without limitation, alteration of the cell surface expression of CD69, CD71, CD25, HLA-DR, and CTLA-4, changes to the cell surface glycosylation profile, translocation from the cytoplasm to the nucleus of transcription factors including NFAT, Rel A and p50, activation of the transcription of a pleiotropic set of genes including the gene encoding the cytokine, IL-2, exit from G0 into stage G1 of the cell cycle and, ultimately, cell proliferation. In one non-limiting embodiment, "activating" of T cells can be demonstrated by upregulation of CD69 and CD25 in the T cells.

(b) In the particular case of thrombin-activated platelet secretion, "activation" means (without limitation) triggering and development of the signaling pathway beginning with stimulation of the PAR1 and PAR4 receptors to stimulate Gq, in turn interacting with and stimulating phospholipase C-β to hydrolyze phosphatidylinositol biphosphate and release inositol trisphosphate and diacyglycerol (DAG), which in turn stimulate calcium mobilization and protein kinase C-mediated protein phosphorylation and CalDAG-GEF1 activity plus additional activities finally resulting in platelet secretion.

In a physiological context, T cell activation is a complex and coordinated sequence of cellular responses to contact of the T-cell with an antigen presenting cell (APC), triggered by the T-cell's T cell receptor (TCR) surface protein binding to antigen-loaded major histocompatibility complex II (MHC-II) proteins on the APC's surface, combined with binding of the T-cell surface protein CD28 to one of two co-stimulatory surface molecules on the APC: CD80 or CD86. These triggering events elicit a complex cascade of T-cell responses, termed activation, beginning with early responses almost instantly upon contact but continuing to unfold into later responses for hours or even days, including alteration of the cell surface expression of proteins including CD69, CD71, CD25, HLA-DR, and CTLA-4, changes to the cell surface glycosylation profile, translocation from the cytoplasm to the nucleus of transcription factors including NFAT, Rel A and p50, activation of the transcription of a pleiotropic set of genes including the gene encoding the cytokine, IL-2, exit from $G_0$ into stage $G_1$ of the cell cycle and, ultimately, cell proliferation.

In a laboratory (as opposed to physiological) context, this same cascade of responses ultimately leading to altered gene expression and proliferation of T-cells can be artificially triggered by contacting quiescent naïve T-cells with anti-CD3 plus anti-CD28 antibodies, in the presence of soluble IL-2 in the medium. These antibodies are more effective triggers of long-lasting and complete activation when they are attached to a solid surface than when they are present free in solution, such as when they are bound to the walls and floor of the culture vessel or to the surface of relatively large (4.5 um diameter; i.e., cell-sized), solid, polymeric microbeads such as ThermoFisher Scientific's Dynabeads®.

Efficient T cell activation is a necessary prerequisite to achieving highly efficient viral transduction of T cells in order to genetically engineer those cells to stably express a transgene. Additionally, the cell proliferation that is a consequence of T cell activation is required in order to expand the genetically engineered cells in order to manufacture an effective dose of cells for a clinical application such as a cellular immunotherapy like KYMRIAH™ or Yescarta™ (typically requiring thousand-fold or higher levels of cell expansion).

One surprising aspect of the present methods is our discovery that anti-CD3/CD28 antibodies are at least as effective at inducing activation when bound to lipid-shell microbubbles as they are in conventional activation reagents wherein the antibodies are bound to solid plastic beads. As shown in the examples, antibody-bearing microbubbles can induce substantially greater activation of T cells (as assessed by growth curves) than do plastic beads bearing these same antibodies. This is surprising because it is accepted in the art that solid bead activating reagents such as Dynabeads® should remain in contact with the cells for an extended period in order to induce levels of activation sufficient to support efficient viral transduction (1-3 days according to the manufacturer), whereas lipid-shell gas-core microbubbles, unlike plastic beads, are labile in culture and are unobservable on cells after just a few hours. Thus, after this time period the microbubbles are collapsed and/or fragmented while the microbubble residua (i.e.: the lipid shell remnants) remain.

In one embodiment, the methods further comprise concentrating the target cells linked to microbubbles in the closed container. Such a concentration step may be carried out via any suitable means within the container, including but not limited to concentrating methods described herein.

In another embodiment, the methods may further comprise collapsing and/or otherwise disrupting the microbubbles after producing the target cells linked to microbubbles. As surprisingly demonstrated in the examples that follow, the microbubbles can be collapsed or otherwise disrupted very shortly after target cell binding without affecting the activation or transduction efficiency ultimately seen using the methods disclosed herein. Any suitable method may be used to collapse and/or otherwise disrupt the microbubbles; in one non-limiting embodiment, the methods may comprise applying positive pressure to actively and irreversibly collapse the gas-filled microbubbles after binding to the target cell.

In one embodiment, the collapsing and/or disrupting the microbubbles occurs after concentrating the target cells linked to microbubbles in the closed container. In another embodiment, the collapsing and/or disrupting the microbubbles occurs within about 180 minutes after initiating the contacting. In various further embodiments, the collapsing and/or disrupting the microbubbles occurs within about 170, 160, 150, 140, 130, 120, 110, 100, 90, 80, 75, 70, 65, 60, 55, 50, 45, 40, 35, 30, 25, 20, 15, 10, 5, 4, 3, 2, or 1 minute after initiating the contacting. In another embodiment, the collapsing and/or disrupting the microbubbles occurs between about 1 minute and about 180 minutes after initiating the contacting. In various further embodiments, the collapsing and/or disrupting the microbubbles occurs between about 2 minutes and about 180 minutes, about 3 minutes and about 180 minutes, about 4 minutes and about 180 minutes, about 5 minutes and about 180 minutes, about 6 minutes and about 180 minutes, about 7 minutes and about 180 minutes, about 8 minutes and about 180 minutes, about 9 minutes and about 180 minutes, about 10 minutes and about 180 minutes, about 11 minutes and about 180 minutes, about 12 minutes and about 180 minutes, about 13 minutes and about 180 minutes, about 14 minutes and about 180 minutes, about 15 minutes and about 180 minutes, about 16 minutes and about 180 minutes, about 17 minutes and about 180 minutes, about 18 minutes and about 180 minutes, about 19 minutes and about 180 minutes, about 20 minutes and about 180 minutes, about 21 minutes and about 180 minutes, about 22 minutes and about 180 minutes, about 23 minutes and about 180 minutes, about 24 minutes and about 180 minutes, about 25 minutes and about 180 minutes, about 26 minutes and about 180 minutes, about 27 minutes and about 180 minutes, about 28 minutes and about 180 minutes, about 29 minutes and about 180 minutes, or about 30 minutes and about 180 minutes after initiating the contacting.

In various further embodiments, the collapsing and/or disrupting the microbubbles occurs between about 1 minute and about 120 minutes, about 2 minutes and about 120 minutes, about 3 minutes and about 120 minutes, about 4 minutes and about 120 minutes, about 5 minutes and about 120 minutes, about 6 minutes and about 120 minutes, about 7 minutes and about 120 minutes, about 8 minutes and about 120 minutes, about 9 minutes and about 120 minutes, about 10 minutes and about 120 minutes, about 11 minutes and about 120 minutes, about 12 minutes and about 120 minutes, about 13 minutes and about 120 minutes, about 14 minutes and about 120 minutes, about 15 minutes and about 120 minutes, about 16 minutes and about 120 minutes, about 17 minutes and about 120 minutes, about 18 minutes and about 120 minutes, about 19 minutes and about 120 minutes, about 20 minutes and about 120 minutes, about 21 minutes and about 120 minutes, about 22 minutes and about 120 minutes, about 23 minutes and about 120 minutes, about 24 minutes and about 120 minutes, about 25 minutes and about 120 minutes, about 26 minutes and about 120 minutes, about 27 minutes and about 120 minutes, about 28 minutes and about 120 minutes, about 29 minutes and about 120 minutes, or about 30 minutes and about 120 minutes after initiating the contacting.

In other embodiments, the collapsing and/or disrupting the microbubbles occurs between about 1 minute and about 60 minutes, about 2 minutes and about 60 minutes, about 3 minutes and about 60 minutes, about 4 minutes and about 60 minutes, about 5 minutes and about 60 minutes, about 6 minutes and about 60 minutes, about 7 minutes and about 60 minutes, about 8 minutes and about 60 minutes, about 9 minutes and about 60 minutes, about 10 minutes and about 60 minutes, about 11 minutes and about 60 minutes, about 12 minutes and about 60 minutes, about 13 minutes and about 60 minutes, about 14 minutes and about 60 minutes, about 15 minutes and about 60 minutes, about 16 minutes and about 60 minutes, about 17 minutes and about 60 minutes, about 18 minutes and about 60 minutes, about 19 minutes and about 60 minutes, about 20 minutes and about 60 minutes, about 21 minutes and about 60 minutes, about 22 minutes and about 60 minutes, about 23 minutes and about 60 minutes, about 24 minutes and about 60 minutes, about 25 minutes and about 60 minutes, about 26 minutes and about 60 minutes, about 27 minutes and about 60 minutes, about 28 minutes and about 60 minutes, about 29 minutes and about 60 minutes, or about 30 minutes and about 60 minutes after initiating the contacting.

In further embodiments, In various further embodiments, the collapsing and/or disrupting the microbubbles occurs between about 1 minute and about 30 minutes, about 2 minutes and about 30 minutes, about 3 minutes and about 30 minutes, about 4 minutes and about 30 minutes, about 5 minutes and about 30 minutes, about 6 minutes and about 30 minutes, about 7 minutes and about 30 minutes, about 8 minutes and about 30 minutes, about 9 minutes and about 30 minutes, about 10 minutes and about 30 minutes, about 11 minutes and about 30 minutes, about 12 minutes and about 30 minutes, about 13 minutes and about 30 minutes, about 14 minutes and about 30 minutes, about 15 minutes and about 30 minutes, about 16 minutes and about 30 minutes, about 17 minutes and about 30 minutes, about 18 minutes and about 30 minutes, about 19 minutes and about 30 minutes, about 20 minutes and about 30 minutes, about 21 minutes and about 30 minutes, about 22 minutes and about 30 minutes, about 23 minutes and about 30 minutes, about 24 minutes and about 30 minutes, about 25 minutes and about 30 minutes, about 26 minutes and about 30 minutes, about 27 minutes and about 30 minutes, about 28 minutes and about 30 minutes, or about 29 minutes and about 30 minutes after initiating the contacting.

In a further embodiment, the activating is achieved without separating the target cells from the microbubbles or microbubble residua. In this embodiment, no steps are taken to separate microbubbles or microbubble residua from the target cells. In this embodiment, for example, the methods may comprise collapsing and/or otherwise disrupting the microbubbles after producing the target cells linked to microbubbles, without any steps being taken to separate the microbubble residua from the target cells.

In one embodiment, the interval between initiating the contacting and initiating the transducing by contacting the activated $CD3^+$ target cells with the genetically engineered viral vector is between about 12 hours and about 36 hours. In this embodiment, the gas-filled microbubbles have substantially or completely depleted themselves within about 3 hours, or may have been actively collapsed or otherwise disrupted even earlier, leaving the microbubble residua. The resulting activation in the substantial or complete absence of the gas-filled microbubbles is very unexpected to those of skill in the art.

T lymphocytes (including naïve $CD3^+$ or $CD4^+$ T lymphocytes and Treg cells) are relatively unique among cell types of wide interest today as candidates for genetically modified cell therapies in their requirement for activation prior to viral transduction. In contrast, such other candidate therapeutic cells as monocyte-derived macrophages, primary natural killer cells, neurons, skin fibroblasts, epithelial cells, keratinocytes, primary hepatocytes, mesenchymal stem cells, and adipose-derived stem cells have all proven to be able to be efficiently transduced without prior activation. Nevertheless, other examples may be offered in which simultaneous cell isolation and activation might be commercially advantageous. One such example (not directly involving therapeutic cells) would be the production of autologous serum or plasma as a cell culture additive for the expansion of autologous stem, progenitor, or immune cells. Platelet-rich plasma is known to be a potent cell culture additive, presumably due to the release of a complex mixture of cytokines and other growth-promoting factors by activated platelets, and the use of autologous serum in the manufacture of autologous cell therapies eliminates the threat of pathogen transmission potentially posed by the more common use of fetal calf serum in cell culture. Unfortunately, activated platelets are extremely 'sticky,' binding to and aggregating other cell types, which can complicate cell analysis and manufacturing processes. Employing the cartridge of U.S. Pat. No. 9,695,394 (hereinafter the '394 patent) with the BACS/activation microbubbles of the present disclosure (in this case, with the buoyant labels attached to soluble collagen fragments, to which platelets bind and which potently activate platelets) for the negative selection and simultaneous activation of platelets, may facilitate the production of autologous serum or plasma fortified with platelet-derived cytokines and other growth-promoting factors but substantially free of platelets themselves.

As used herein, a "host liquid" is a fluid (including but not limited to whole blood, placental/cord blood, bone marrow, leukapheresis, etc.) containing target cells, admixed with non-target cells. The host liquid may be diluted or undiluted (for example, diluted with buffers or any other liquid useful in isolating desired cells, such as saline, phosphate buffered saline, a cell culture medium, a protease solution, etc.). In one embodiment, the host liquid is peripheral blood, cord blood, or leukapheresis product, or diluted versions thereof. In another embodiment, the host liquid may comprise a suspension of harvested cells (including but not limited to T cells (such T cells including but not limited to CD3+, CD4+, and Treg cells) that have been cultured in vitro.

In one embodiment, the host liquid may be a "non-depleted" host liquid, in that all cells normally present in the relevant host liquid, or dilution thereof, remain present. In another embodiment, the host liquid may comprise a depleted host liquid. A "depleted" host liquid is a host liquid, or dilution thereof, from which a substantial fraction (for example, at least 50%; in other embodiments, at least 60%, 70%, 75%, 80%, 85%, 90%, 91%, 92%, 93%, 94%, 95%, 96%, 97%, 98%, 99%, or more) of one or more types of non-target cells have been depleted. By way of non-limiting examples, a depleted host liquid may comprise target cells in suspension after depletion of red blood cells from whole blood via density centrifugation, differential centrifugation, or lysis, or from which red blood cells and granulocytes have been depleted, or from which platelets have been depleted. In all embodiments of depleted host liquid, the target cells may be suspended in any suitable liquid, including but not limited to saline, phosphate buffered saline, a cell culture medium, diluted or undiluted original host liquid (i.e.: whole blood, etc.).

The lipid shell of the microbubbles may comprise lipids or phospholipids. In one embodiment, the gas-filled bubbles comprise perfluorocarbon gas cores encompassed by a phospholipid shell. In any of these embodiments, the gas-filled bubbles may have any suitable diameter; in one non-limiting embodiment, the gas-filled bubbles have a diameter between about 1 um and about 6.5 um.

The gas-core lipid-shelled microbubbles, or the target cells, display one or more antibodies or ligands that bind to cell surface molecules on the target cells. Thus, the choice of the one or more antibodies or ligands will depend on the target cell(s) of interest. The antibody or ligand may be directly bound to the microbubbles or may be attached via any suitable linker. As used herein, "linker" (or, individually "a linker") comprises a pair of chemical moieties (a first linker and a second linker) attached covalently or non-covalently one to an antibody or linker, and the other to the microbubble, which are able to spontaneously attach (either covalently or non-covalently) to each other in a suitable medium under suitable conditions with sufficiently high affinity to achieve the indirect connection of the antibody to a microbubble, via the linkers. In certain embodiments, the at least one first linker moieties are functionally exposed avidin or streptavidin, and the second linker moieties are biotin or a biotin derivative. In other embodiments, the first linker is a first oligonucleotide and the second linker is a second oligonucleotide complementary over at least a portion of its length (such as fully complementary) to the first oligonucleotide and capable of binding to the first oligonucleotide via base pairing.

The antibodies may be bound to the microbubbles or target cells prior to introduction into the closed system, or may be introduced into the closed system together with or preceding the microbubbles and/or cells under conditions to promote binding of the antibodies to the cells and to the microbubbles within the closed system.

In another embodiment, the methods further comprise transducing the activated target cells with a vector, such as a viral vector, comprising a transgene to produce transduced target cells, wherein the transducing comprises contacting the activated target cells with gene transduction reagents comprising a vector comprising a transgene under conditions suitable to transduce the activated target cells. In one such embodiment, the transducing is carried out in the closed system. Methods for transduction are well known in the art; thus, any suitable transgene (including but not limited to a chimeric antigen receptor) may be transduced into the target cells as deemed appropriate. Any suitable transgene-bearing vector may be used, including but not limited to viral vectors (such as retroviral vectors). Any culture conditions may be used as deemed suitable in light of the specific cell population and other relevant factors. In this embodiment, the methods permit efficient transduction with a transgene-bearing vector (including but not limited to a retroviral vector), thus enabling a dramatically simplified 'one pot' manufacturing process for transgenic target cells (such as lymphocytes), from the starting product (such as leukapheresis product or peripheral blood) to transgene-expressing target cells, with high overall efficiency (target cell recovery and transduction) at low capital cost. Non-limiting embodiments of transduction are provided in the examples that follow.

In one embodiment, the transduction comprises activated $CD3^+$ cells being contacted with a genetically engineered adenovirus or lentivirus vector containing an artificial gene construct encoding a chimeric (two-part) transmembrane fusion protein comprising an extracellular anti-CD19 single chain antibody fragment and intracellular T cell signaling (CD3-ζ) and co-stimulatory (4-1BB) domains (the so-called chimeric antigen receptor, or CAR), and the resulting transduced cells are CAR-T cells.

In another embodiment, the methods further comprise expanding the activated target cells or the transduced target cells, wherein the expanding comprises culturing the activated target cells or the transduced target cells under conditions suitable to promote proliferation of the activated target cells or the transduced target cells. In one such embodiment, the expanding is carried out in the closed system. Any culture conditions may be used as deemed suitable in light of the specific cell population and other relevant factors. Practitioners skilled in the art will recognize that the transduced cells produced by the methods of this disclosure can subsequently be transferred to a separate cell culture system (such as a bioreactor, culture flasks, or rocking bag reactor) for final cell expansion. In one embodiment, the cells that have been isolated, activated, and transduced within a single container such as the '394 patent's cartridge are subsequently expanded within that same single container rather than in an external culture system, thus providing a complete one-pot manufacturing system from blood pre-processing through cell expansion. In one embodiment of this aspect of the disclosure, the gas headspace over the culture medium in the single container is charged once with 5% $CO_2$ in air at the beginning of the cell expansion process, and the volume of the headspace is sufficient to support expansion of the cells, without further headspace flushing, to the point at which splitting of the cells into one or more additional closed containers is required. In another embodiment, the single container's headspace is charged more than once before the cells are split. In another embodiment, the headspace is continuously flushed with humidified 5% $CO_2$ in air. In a preferred embodiment, the expanding cells are split into additional cartridges of the '394 patent aseptically via sterile connections, thus enabling 'one (type of) pot' manufacturing to continue through cell harvest, washing, and suspension in the medium in which they will be shipped back to the physician. In another embodiment, the single container such as a cartridge of the '394 patent is incubated on its side, or while inverted, to maximize the air/fluid interface area across which gas exchange occurs. In another embodiment the incubated single container is gently rocked, rolled, or otherwise agitated to promote gas exchange.

In a further embodiment, the methods further comprise harvesting the expanded activated target cells or transduced target cells to produce a harvested activated cell population or a harvested transduced cell population, wherein the harvesting is optionally carried out in the closed container. Any harvesting steps and conditions may be used as suitable for an intended use of the activated cell population or a harvested transduced cell population. In one embodiment, the methods may further comprise washing the harvested activated cell population or the harvested transduced cell population, wherein the washing is optionally carried out in the closed container. In another embodiment, the methods may further comprise transferring the harvested activated cell population or the harvested transduced cell population to a medium suitable for infusion (for immediate use), or to a cryopreservation medium (for later use), wherein the transferring is optionally carried out in the closed container. Any suitable media for infusion may be used, as deemed appropriate by attending medical personnel based on all relevant factors. Similarly, any cryopreservation media may be used as deemed appropriate in light of the specific cell population, ultimate intended use, and other relevant factors.

In a specific embodiment of the methods of the disclosure:
  (a) the target cells are human CD3+ T lymphocytes;
  (b) the host liquid comprises a liquid compatible with buoyancy-activated cell sorting, such as (without limitation) phosphate buffered saline;
  (c) the host liquid contains a suspension of PBMCs,
  (d) the host liquid's PBMCs are prepared from either
    (i) diluted or undiluted blood,
    (ii) diluted or undiluted leukapheresis product, or
    (iii) diluted or undiluted bone marrow;
  (e) the one or more antibodies comprise:
    (i) an anti-CD3 antibody, and
    (ii) an anti-CD28 antibody;
  (f) the antibodies are present on the surface of the microbubbles in a ratio of one or more anti-CD28 antibody molecule per anti-CD3 antibody molecule;
  (g) only a single contacting of the target cells by the microbubbles (one of which is bound to the antibodies) is required to achieve a degree of target cell activation sufficient to support efficient viral transduction of the target cells with a synthetic gene encoding a chimeric antigen receptor, and
  (h) subsequent contacting of the isolated cells with a viral vector comprising a transgene achieves efficient transduction of the isolated cells without prior removal of the microbubbles or their residua.

In a further specific embodiment, the steps of leukapheresis or blood pre-processing, target cell isolation via BACS, cell activation, cell transduction and all required cell washing steps all occur in a single container, such as a single cartridge of U.S. Pat. No. 9,695,394, thus comprising a one-pot manufacturing process.

In all embodiments of the methods disclosed herein, the closed system may be any suitable closed system. In one embodiment, the closed system is as disclosed in U.S. Pat. No. 9,695,394. FIG. 1 illustrates an example closed system 100. As shown in FIG. 1, the closed system 100 may include a cartridge 102, a control module 104, and a docking station 106. As used herein, "cartridge" is a closed housing (having a roof) that allows the aseptic transfer of cells between containers within the closed housing and the mixing of cells, antibodies or ligands, and microbubbles to accomplish linkage, comprising three or more mechanically joined containers which are transiently fluidically connected. The cartridge 102 may hold up to 250 mL of liquid, may be cylindrical, may be single-use, and may be constructed preferably of hard plastic, and more preferably optically clear polycarbonate. In certain other embodiments, the cartridge 102 is reusable. The control module 104 may be removably coupled to the cartridge 102. The control module 104 is an electro-mechanical device with optical and gravitational sensing. In particular, the control module 104 provides optical sensing of cell interfaces in the bottom of the cartridge 102, and may be configured to control one or more reversible closing devices to control activity between various containers of the cartridge 102, as discussed in additional detail below. The docking station 106 may be removably coupled to the control module 104, and may be used to recharge the control module 104. Further, the docking station 106 may receive one or more protocols wirelessly or through a wired connection, and may further be configured to download and process data received by the control module 104. The docking station 106 preferably uses a rechargeable battery system to power the control module 104 that monitors and controls gravitational and optical sensing equipment and directs activity in the cartridge 102. The means for determining a G force may be any commonly known in the art, such as calculating said force through a measurement of centrifuge RPM, or through direct measurement of acceleration or force.

When the cartridge 102 is removably attached to the control module 104, one or more detectors, such as optical sensors or other sensors of the control module 104 may be used to detect the type of cells flowing through the cartridge 102. Further, the control module 104 may also include at least one but preferably two or more optical or other emitters. In an exemplary embodiment, four infrared emitters/detector pairs are arranged vertically in the control module 104. In a preferred embodiment, infrared sensors are located directly across from paired infrared emitters. In second preferred embodiment, transmitters that provide wavelengths that are preferentially absorbed by red cells are located directly across from paired sensors sensitive to that frequency. In a third preferred embodiment sensors are utilized that identify cells that have absorbed fluorescent dyes. In the first preferred embodiment, the presence of cells interferes with the emitted infrared light and the infrared light detector quantifies the amplitude of the signal penetrating the fluid. In a preferred embodiment the sensors may assign the level of transmission a value from 0-1000. Pure plasma, which similar to water blocks none of the infrared light, will register a value of roughly 1000. As compacted RBCs pass between the sensor/emitter pairs, essentially all infrared light is blocked and the detector registers a value of 0.

Figure 2:
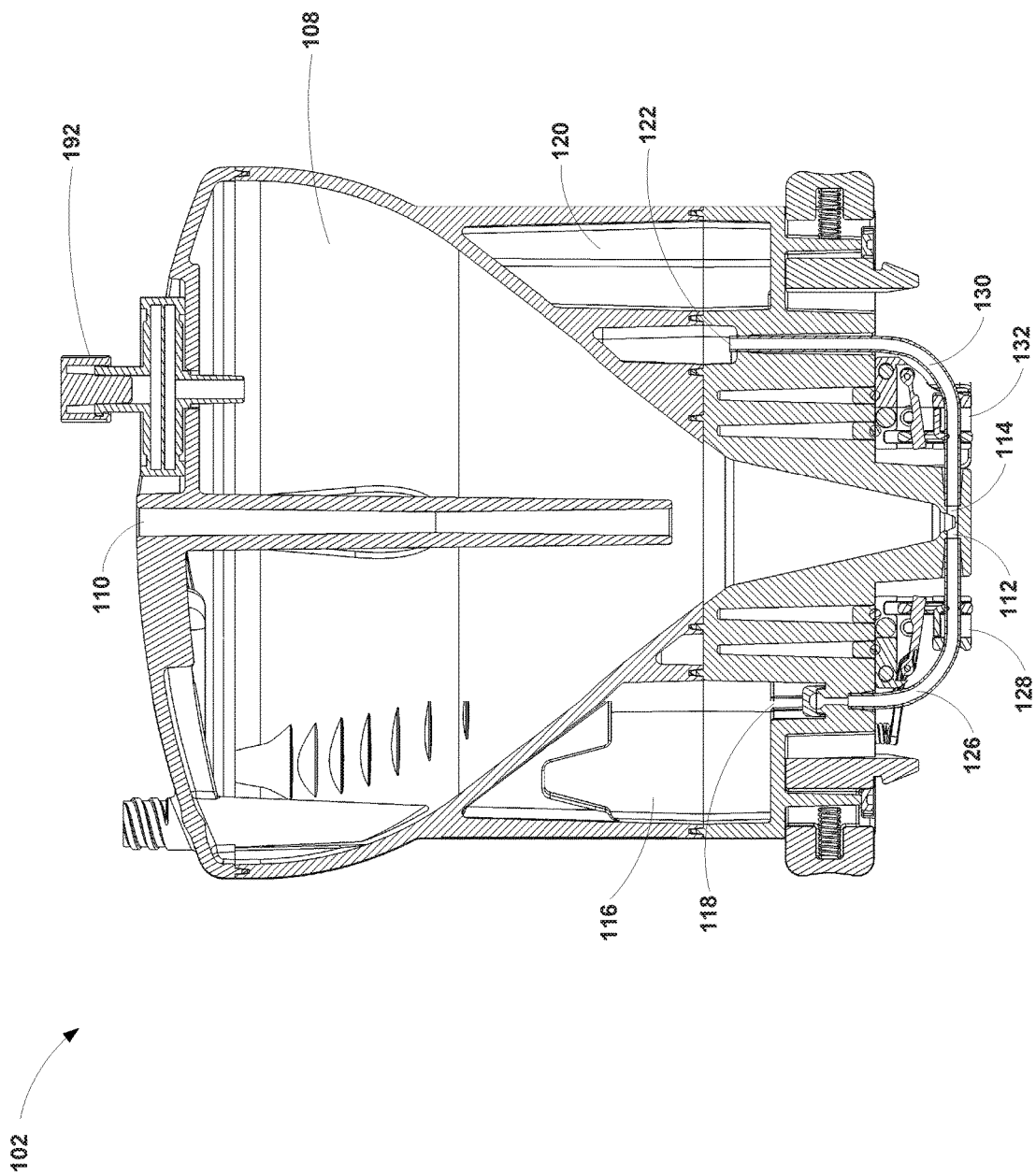
FIG. 2 is a cross-section view of a cartridge of a closed system, according to an example embodiment.

FIG. 2 illustrates a cross-section view of the cartridge 102. As shown in FIG. 2, the cartridge 102 includes a processing container 108 comprising at least one input port 110, a first exit port 112, and a second exit port 114. The cartridge 102 also includes a second container 116 comprising an input port 118, and a third container 120 comprising an input port 122 and a first exit port 124. As described in the process below, a biological fluid containing cells, such as normal blood, cord blood or bone marrow, is delivered to the processing container 108 through the at least one input port 110. The second container 116 of the cartridge 102 comprises a large first rigid storage compartment or RBC depletion compartment, and the third container 120 comprises a smaller second rigid storage compartment or SC compartment into which the WBCs and substantially all the SPCs are transferred. The second container 116 is significantly larger than the third container 120, as the volume of RBCs depleted from a blood sample is always much greater that the volume of WBCs collected. All compartments are distinct from one another within the cartridge 102, but contiguous with respect to airflow. The second compartment 116 and the third compartment 120 may be connected by small filtered or sufficiently narrowed air vents to the processing container 108 so as to allow displacement of air as cell solutions move from the processing chamber 108 into the second and third containers 116, 120, but does not permit fluid transfer between the containers. In one embodiment, the processing container 108 is an approximately conical central container, while the second and third containers 116, 120 are smaller, circumferentially located containers. The containers may be of any suitable volume for a given purpose. In one embodiment, the third and second containers 116, 120 each may further comprise additional, normally closed ports providing optional points of connection to any suitable receiving containers external to the cartridge 102 for gravity draining or as a result of adding air pressure through the air filter 192. In a further embodiment, fluid in the processing container 108 may be removed through the internal input tube 110 by the application of air pressure through air filter 192 with that ceases when the level of fluid in the container drops below the lowest point on the internal rigid input tube 110.

As shown in FIG. 2, the cartridge 102 also includes a first conduit 126 connecting the first exit port 112 of the processing container 108 and the input port 118 of the second container 116. The first conduit 126 comprises a first reversible closing device 128. The second container 116 is transiently fluidically connected to the processing container 108 such that fluid flow only from the processing container 108 to the second container 116 may occur when the first reversible closing device 128 is opened. The cartridge 102 also includes a second conduit 130 connecting the second exit port 114 of the processing container 108 and the input port 122 of the third container 120. The second conduit 130 comprises a second reversible closing device 132. The third container 120 is transiently fluidically connected to the processing container 108 such that fluid flow only from the processing container 108 to the third container 120 may occur when the second reversible closing device 132 is opened.

As used herein, a "reversible closing device" is any device that can be closed (such as a by a controller) to prohibit fluid flow. Exemplary such devices include, but are not limited to valves, clamps, and stopcock. As used herein, "transiently fluidically connected" means that the containers are fluidically non-continuous (that is, each functionally closed) other than when transiently connected via opening of the device's normally closed valves to achieve aseptic transfer of fluid or cell suspension from one container to another. The "conduits" may be any suitable device to permit fluid transfer between the containers, including but not limited to tubing. All of the conduits become "normally closed", such that the containers are not fluidically connected, as soon as the operator removes a pin installed during cartridge assembly that prevents the conduits from being closed. The conduits may be closed by any suitable reversible closing device, such as a valve, clamp or stopcock. In one embodiment, the conduits within the cartridge may be closed by a spring loaded, tube pinching mechanism at all times except when fluids should pass, at which time the pinching mechanism may be rotated (for example, by a control module automatically controlling the reversible opening of the conduit) to allow passage of the fluids, and then may be rotated again to allow the spring loaded tube pinching mechanism to close off that passage by re-pinching the conduit. In such an example, the reversible closing devices comprise two opposing clamps having pinching surfaces approximately 0.088 inches wide, and require approximately 1.6 pounds of pinching force to block all fluid passage through a urethane tube with an inner diameter of 0.062 inches and an exterior diameter of 0.088 inches when the hydraulic pressure in the tube is at 325 PSI. Pinching forces in excess of 1.6 pounds may be required at greater pressures, and reduced pinching forces may be sufficient at lower pressures. In such an example, a cantilever system may be used to achieve these required pinching pressures. The cantilever system may open and close the conduits (pinch and release the tubing) as needed. Springs may be provided on each cantilever, and are preferably located at the extreme end of the cantilever. The actuator overcomes the resistance of the springs to move the lever. Once the actuator stops applying force, the bias of the springs urges the lever back to its first position.

As described above, the processing container 108, or other containers may optionally be interrogated by at least one detector for detecting the presence or absence of cells. In such an embodiment, the control module 104 controls opening and closing of the first reversible closing device 128 and/or the second reversible closing device 132 based on information relayed from the at least one detector. Any suitable detector may be used, including but not limited to optical detectors, as discussed above in relation to FIG. 1.

As will be described in detail below, in operation, the RBCs initially migrate towards the bottom of the processing container 108, moving radially outward away from the axis of rotation of the centrifuge until reaching the bottom of the processing container 108, where the first reversible closing device 128 and the second reversible closing device 132 reside. Here, the pressure head of fluid above the bottom of the processing container 108 urges the fluid into one of two compartments: either the second container 116 or the third container 120. Which compartment the fluid is directed into is dependent upon the status (open, closed) of the first reversible closing device 128 and the second reversible closing device 132. In either case, after passing through the first reversible closing device 128 and/or the second reversible closing device 132, the fluid flows generally toward the axis of rotation, urged by pressure from the of fluid (mostly plasma) remaining in the processing container 108. The fluid that has passed through the first reversible closing device 128 and/or the second reversible closing device 132 is then retained in either the second container 116 or the third container 120. Through minute adjustments of the first reversible closing device 128 and/or the second reversible closing device 132, unwanted cell solutions may be depleted and desired cell solutions may be harvested.

Figure 3:
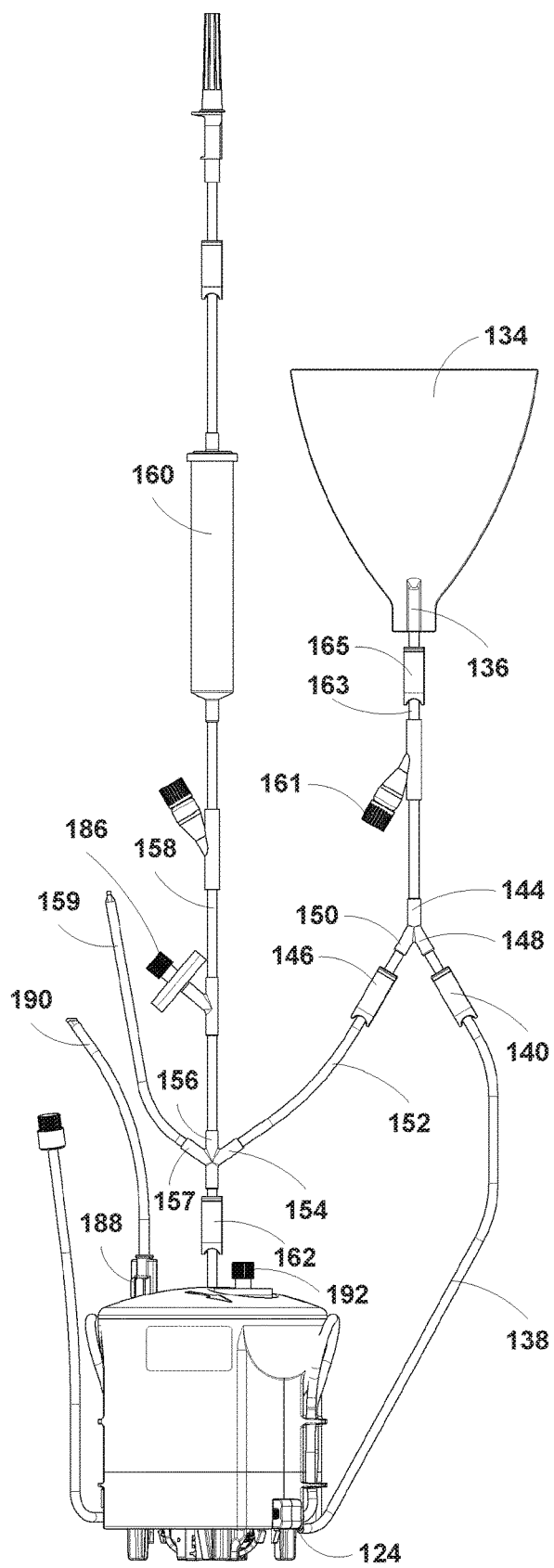
FIG. 3 is a side view of a closed system, according to an example embodiment.

As shown in FIG. 3, the closed system 100 may further include a transfer container 134 comprising at least one port 136. The transfer container 134 may be mechanically coupled to the cartridge 102, or may be physically connected only via the relevant conduit connecting the transfer container 134 to containers within the cartridge 102 to maintain the system as a closed system. As such, in one embodiment, the transfer container 134 is internal to the cartridge 102; in another embodiment the transfer container 134 is external to the cartridge 102. The various containers may comprise any suitable material, such as a rigid structure, a bag, a bottle, or any other suitable structure. In one embodiment, each container is a rigid container, such as a hard plastic container (including but not limited to polycarbonate). In another embodiment, the transfer container 134 is a flexible container, including but not limited to a bag. The transfer container 134 can be a rigid container, because the air in the container at the start of the transfer of harvested target cells in solution can displace along the relevant conduit connecting it to the processing container. The transfer container 134 also can be a flexible container, which has the advantage of being foldable into a small shape to make it easier to store, for example, in the rotor compartment of a centrifuge during centrifugation.

Further, as shown in FIG. 3, the closed system 100 further includes an at least third conduit 138 connecting the first exit port 124 of the third container 120 to the at least one port 136 of the transfer container 134, and the at least one port 136 of the transfer container 134 to the at least one input port 110 of the processing container 108. The at least third conduit 138 comprises at least a third reversible closing device 140, such that the third container 120 is transiently fluidically connected to the transfer container 134, and the transfer container 134 is transiently fluidically connected to the processing container 108. The at least third conduit 138 is configured such that only one of the following may be true: (I) fluid flow only from the third container 120 to the transfer container 134 may occur when the at least third reversible closing device 140 is opened, or (II) fluid flow only from the transfer container 134 to the processing container 108 may occur when the at least third reversible closing device 140 is opened.

The third conduit 138 between the first exit port 124 of the third container 120 to the transfer container 134 and from the transfer container 134 to the at least one input 110 of the processing container 108 is also normally closed by any suitable reversible closing device. In one embodiment, the third conduit 138 may be clamped on the exterior of the cartridge 102 by the third reversible closing device 140 (just adjacent to the first exit port 124 of the third container 120) and may be unclamped at the time of transfer of sequestered attached cells from the third container 120 to the transfer container 134 (for example, by gravity draining the sequestered attached cells from the third container 120 to the transfer container 134). Following transfer into the transfer container 134, the third reversible closing device 140 on the third conduit 138 adjacent to the third container port 124 may be re-clamped. At that time, for example, the sequestered attached cells may be transferred to the processing container 108 via the third conduit 138 (for example, by gravity draining the sequestered attached cells back into the processing chamber 108, for further processing—such as isolating/enriching a sub-population of the sequestered, attached cells, including but not limited to mononuclear cells to join the cell-free and platelet free plasma from the host liquid). The transfer container 134 therefore provides an economic advantage as the cartridge 102 may be reused.

Additionally, the transfer container 134 allows for improved mixing the target cell suspension and BACS reagents.

The closed system 100 may further include a control module 104, as discussed above in relation to FIG. 1. The control module 104 may be configured to control activity in at least the cartridge 102, and the first and second conduits 126, 130. In some embodiments, the control module 104 may also control activity within the transfer container 134 and/or within the third conduit 138. For example, the control module 104 may control activity within the transfer container 134 and/or within the third conduit 138 in embodiments in which the transfer container 134 is present within the cartridge 102. The control module 104 may control the reversible closing devices 128, 132, 140 that direct the flow of fluid between the cartridge containers 108, 116, 120, such as when placed in a centrifuge. In one non-limiting embodiment, the cartridge 102 containing the target cell/microbubble mixture is centrifuged so that target cells that bind to the microbubbles separate from the cells not bound to the microbubbles. The control module 104 may be programmed to deliver the non-microbubble-bound pelleted cells to the second container 116 of the cartridge 102 via the first reversible closing device 128, leaving the bulk of the supernatant and substantially all of the target cells that bound to the microbubbles in the processing container 108 of the cartridge 102.

In one embodiment, the at least third conduit 138 comprises a single conduit. In this embodiment, the only a single conduit is fluidically coupled to the transfer container 134, and the conduit can be fluidically separated such that fluid flowing from the third container 120 to the transfer container 134 is separated from fluid flowing from the transfer container 134 to the processing container 108. Any suitable reversible closing means can be used in this embodiment. One non-limiting example is shown in FIG. 3, in which the at least third conduit 138 comprises a T or Y connector 144 disposed between the third container 120 and transfer container 134, and between the transfer container 134 and the processing container 108, with appropriate reversible closing devices 140, 146 to regulate the desired fluid flow.

In a further embodiment, the at least one port of the transfer container comprises a first input port 148 and an exit port 150. In this embodiment, the at least third conduit 138 may comprise (i) a third conduit 138 connecting the exit port 124 of the third container 120 to the input port 136 of the transfer container 134, wherein the third conduit 138 comprises a third reversible closing device 140, such that the third container 120 is transiently fluidically connected to the transfer container 134 such that fluid flow only from the third container 120 to the transfer container 134 may occur when the third reversible closing device 140 is opened, and (ii) a fourth conduit 152 connecting the exit port 136 of the transfer container 134 to the at least one input port 110 of the processing container 108, wherein the fourth conduit 152 comprises a fourth reversible closing device 146, such that the transfer container 134 is transiently fluidically connected to the processing container 108, such that fluid flow only from the transfer container 134 to the processing container 108 may occur when the fourth reversible closing device 146 is opened. In this embodiment, separation of fluid flowing from the third container 120 to the transfer container 134 away from fluid flowing from the transfer container 134 to the processing container 108 is made possible by the use of completely separate conduits 138, 152.

In a still further embodiment, the at least one input port 110 of the processing container 108 comprises a first input port 154 and a second input port 156, wherein the at least third conduit 138, or the fourth conduit 152 (when present), connects the exit port 136 of the transfer container 134 to the first input port 154 of the processing container 108. In such an example, the closed system 100 may further comprise a first medium input conduit 158 connecting the second input port 156 of the processing container 108 to at least one medium reservoir 160, wherein the first medium input conduit 158 comprises at least a fifth reversible closing device 162, wherein the at least one medium reservoir 160 is transiently fluidically connected to the processing container 108 such that fluid flow only from the at least one medium reservoir 160 to the processing container 108 may occur when the at least fifth reversible closing device 162 is opened.

The medium input reservoir(s) 160 can be used to supply host liquid, target cells, antibodies or ligands, and/or microbubbles to the processing container 108 via the second input port 156.

In yet another embodiment, the at least one input port 110 of the processing container 108 comprises a third input port 157. The third input port 157 may be coupled to a fifth conduit 159. In such an example, liquid can be removed from the processing chamber 108 by providing positive pressure at the filter 186.

In one embodiment, the at least one port of the transfer container 134 further comprises a second input port 161. For example, the closed system 100 may further comprise a second medium input conduit 163 connecting the second input port 161 of the transfer container 134 to at least one medium reservoir (not shown), wherein the second medium input conduit 163 comprises at least a sixth reversible closing device 165, wherein the at least one medium reservoir is transiently fluidically connected to the processing container 108 such that fluid flow only from the at least one medium reservoir to the transfer container 134 may occur when the at least sixth reversible closing device 165 is opened.

The media input reservoir(s) can be used to supply host liquid, target cells, antibodies or ligands, and/or microbubbles to the transfer container 134 via the second input port 161. In embodiments where at least one medium reservoir is transiently fluidically connected to both the processing container 108 and the transfer container 134, the media reservoir(s) may be the same reservoirs, or each container may have its own dedicated reservoir(s).

In a further embodiment, the closed system 100 further comprises a mixer. The mixer may be used, for example, to promote/improve mixing of (a) the microbubbles and the host liquid, and/or (b) the target, antibodies or ligands, and linkers (when present). In one embodiment, the mixer is a static mixer. A static mixer comprises container with an input and exit that remains stationary while providing continuous mixing of two fluids simultaneously passing through the container, in a configuration such as, but not limited to, a cylindrical tube containing mixer elements oriented throughout the interior length of the cylindrical tube.

Figure 4B:
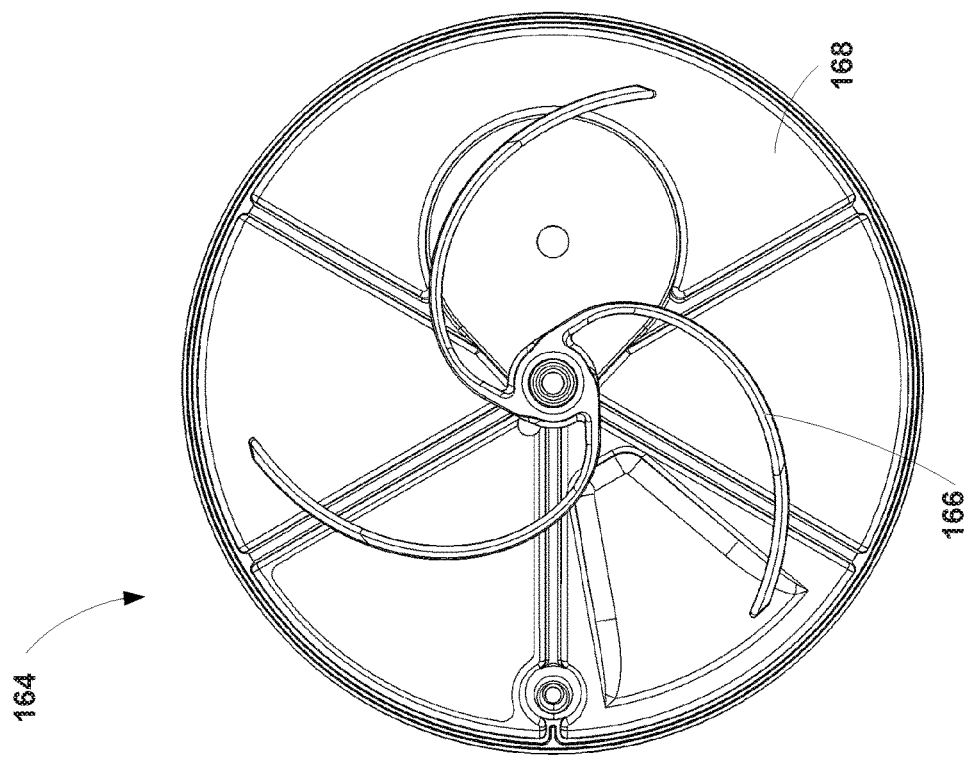
FIG. 4B is a bottom view of the example static mixer of FIG. 4A, according to an example embodiment.
Figure 4A:
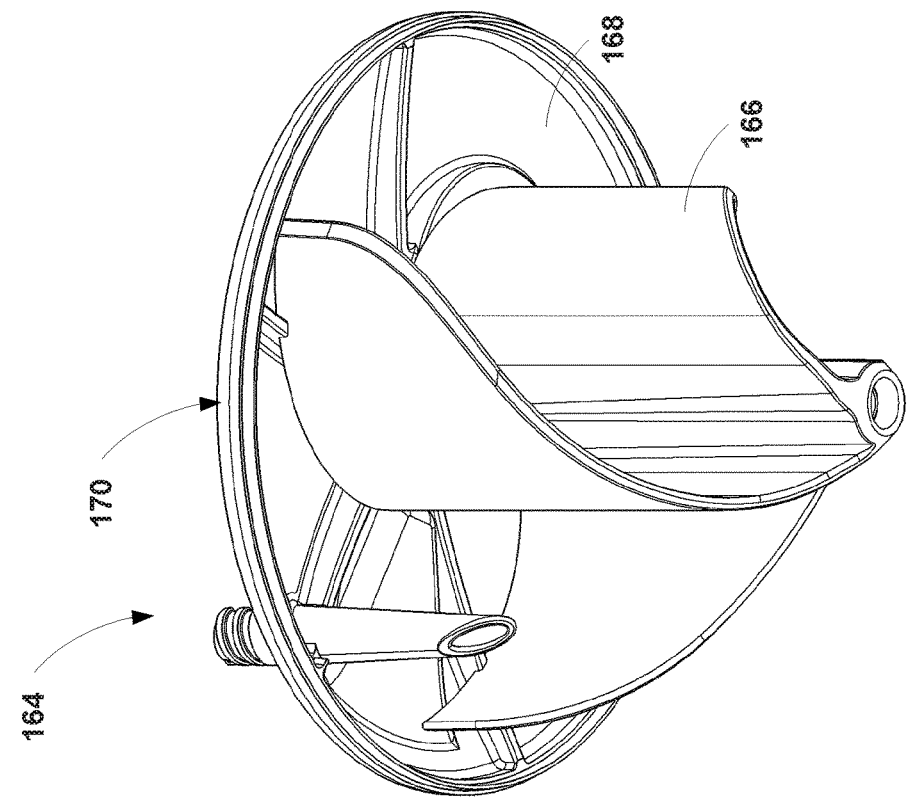
FIG. 4A is a perspective view of an example static mixer on the roof of the cartridge, according to an example embodiment.

Exemplary static mixers appropriate for mixing in the devices of the invention (such as mixing a target cell suspension (major component) and BACS reagents (additive)) are shown in FIGS. 4A-5B. The medium reservoirs described above may be transiently fluidically connected to the static mixer via the fifth and sixth reversible closing devices. In one non-limiting embodiment, as shown in FIGS. 4A and 4B, the static mixer 164 acts to rotate the cartridge 102 on its axis by including an impeller 166 affixed to the internal surface 168 of the cartridge roof 170 causing, for example, a BACS reagent and target cells in solution within the processing container to admix. The advantage of the design in FIGS. 4A-4B is that the mixing addition to the interior of the cartridge is glued in place, so mixing of the in cell solution and the BACS reagents occurs merely by placing the loaded cartridge on a roller table device for a programmable time.

Figure 5B:
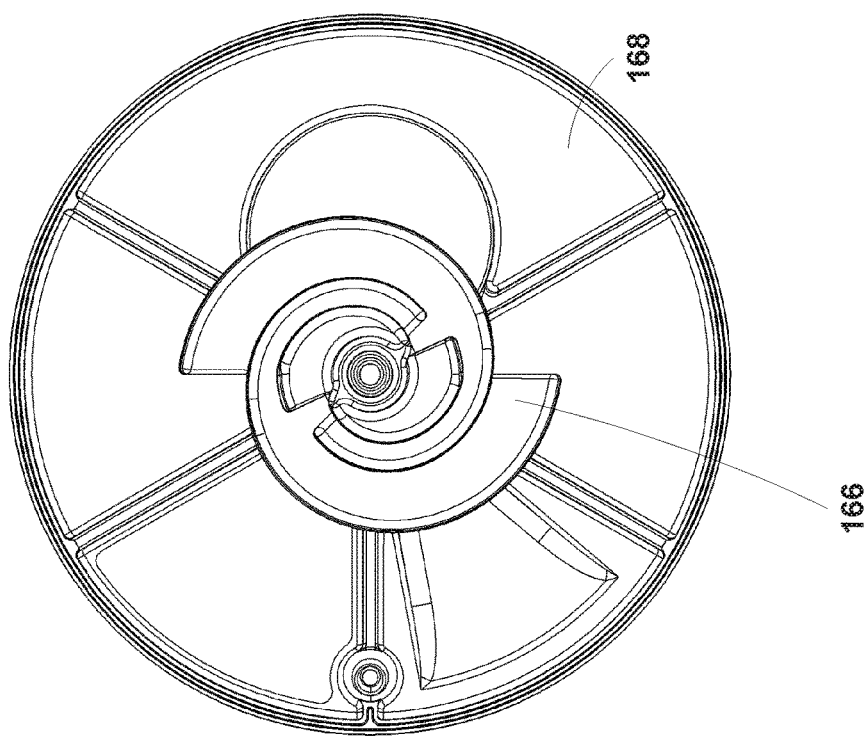
FIG. 5B is a bottom view of the example static mixer of FIG. 5A, according to an example embodiment.
Figure 5A:
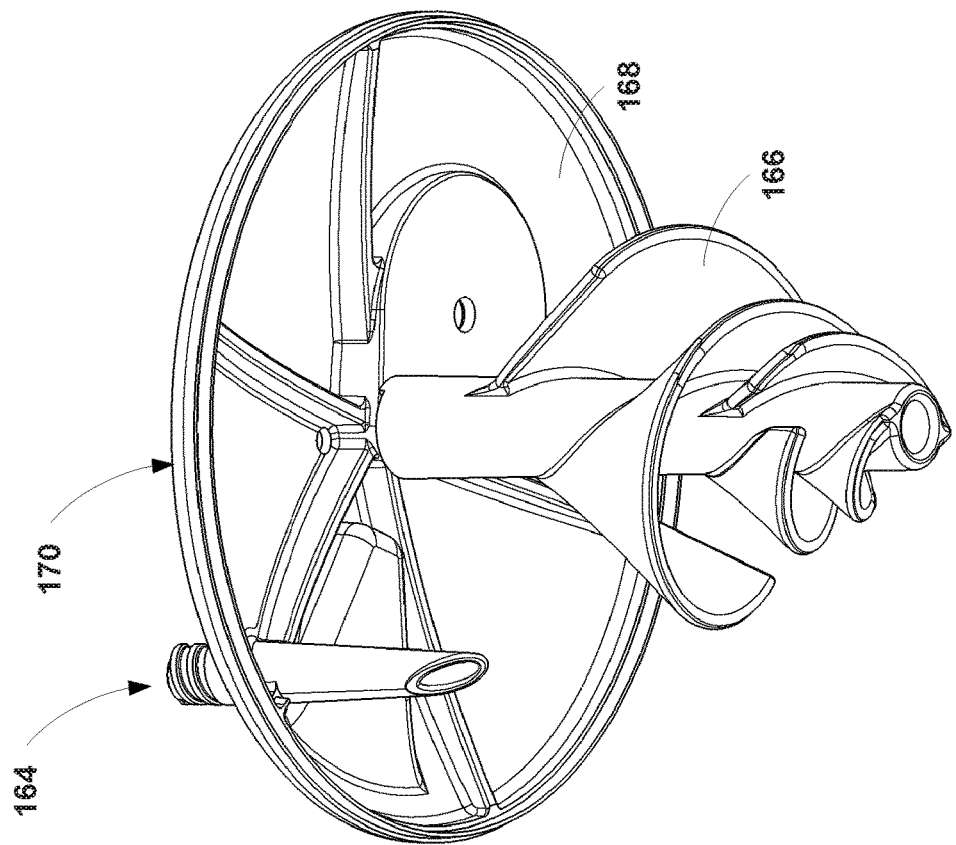
FIG. 5A is a perspective view of another example static mixer on the roof of the cartridge, according to an example embodiment.

In another non-limiting embodiment, as shown in FIGS. 5A and 5B, the static mixer 164 acts to rotate the cartridge 102 on its axis by including an impeller 166 spaced away from the internal surface 168 of the cartridge roof 170 causing, for example, a BACS reagent and target cells in solution within the processing container to admix. The advantage of the design in FIGS. 5A-5B is that the mixing addition to the interior of the cartridge rotates on its axis, driven by a motor means, so that the cartridge remains upright and does not have to be removed from the centrifuge.

Figure 6:
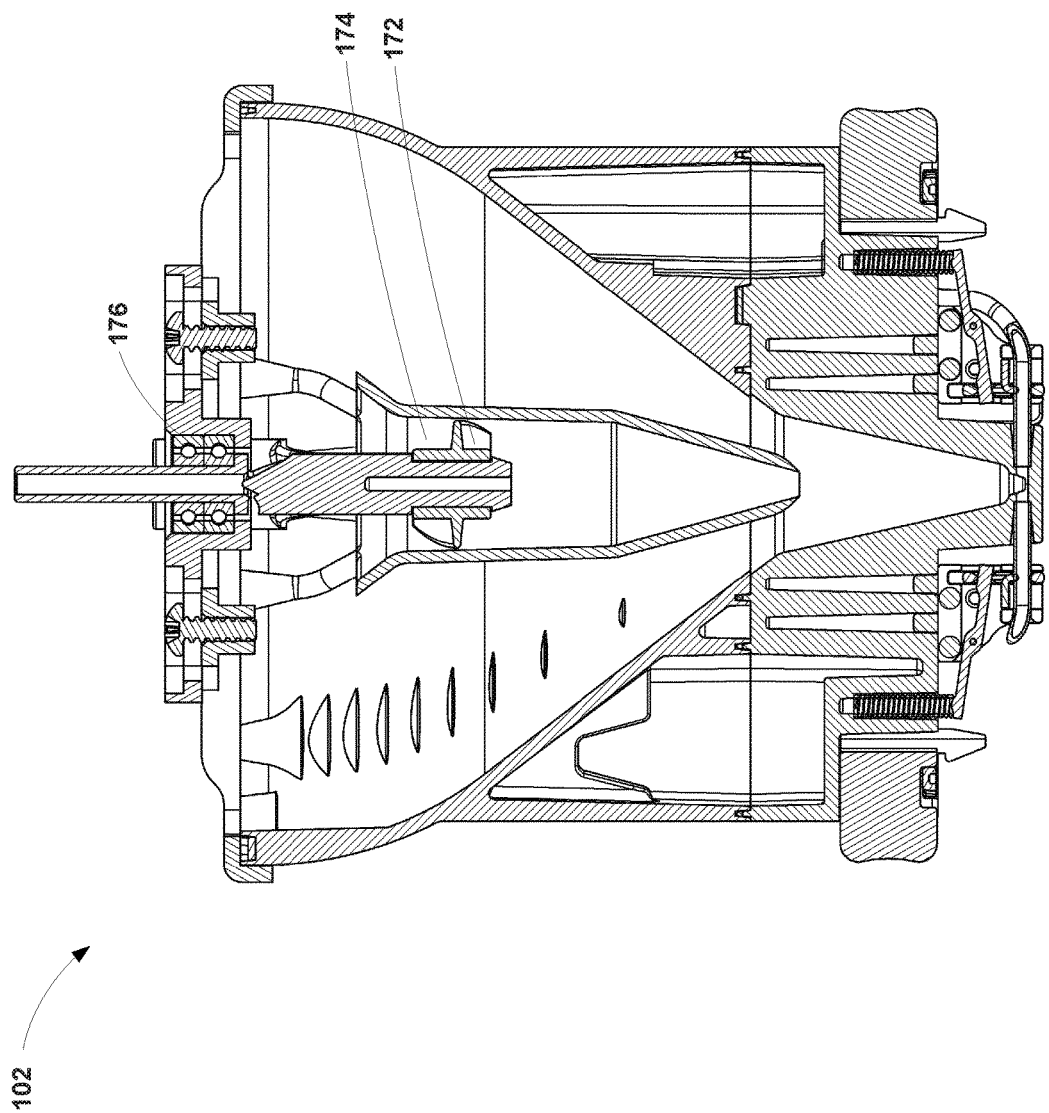
FIG. 6 is a cross-section view of an example mixer in the funnel of the cartridge, according to an example embodiment.

In another non-limiting embodiment, as shown in FIG. 6, the mixer acts to impart circulating motion to an admixture of BACS reagent and target cells in solution within the processing container 108 of the cartridge 102 while the cartridge 102 remains motionless. Such an embodiment may include an impeller 172 positioned within a cylindrical tube 174, with a motor 176 configured to drive the impeller 172 to thereby cause the mixing in the processing container 108.

Figure 7:
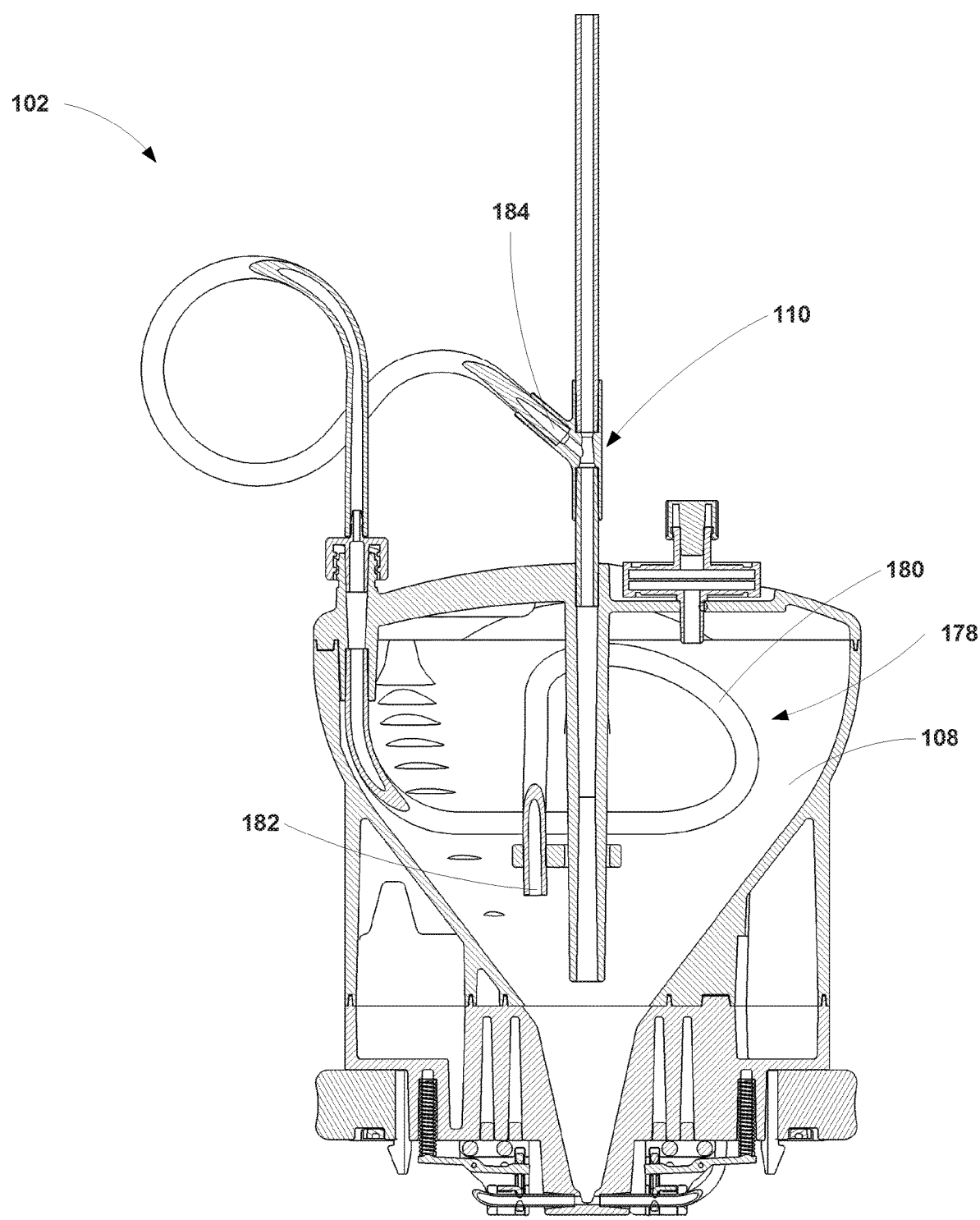
FIG. 7 is a cross-section view of an example peristaltic pump of the cartridge, according to an example embodiment.

In another non-limiting embodiment, as shown in FIG. 7, the mixer comprises a peristaltic pump 178 comprising a pump conduit 180 having a first end 182 and a second end 184, wherein the first end 182 of the pump conduit 180 is positioned in the processing chamber 108, and wherein the second end 184 of the pump conduit 180 is positioned outside of the processing chamber 108 and is connected to the at least one input port 110 of the processing chamber 108.

Figure 8:
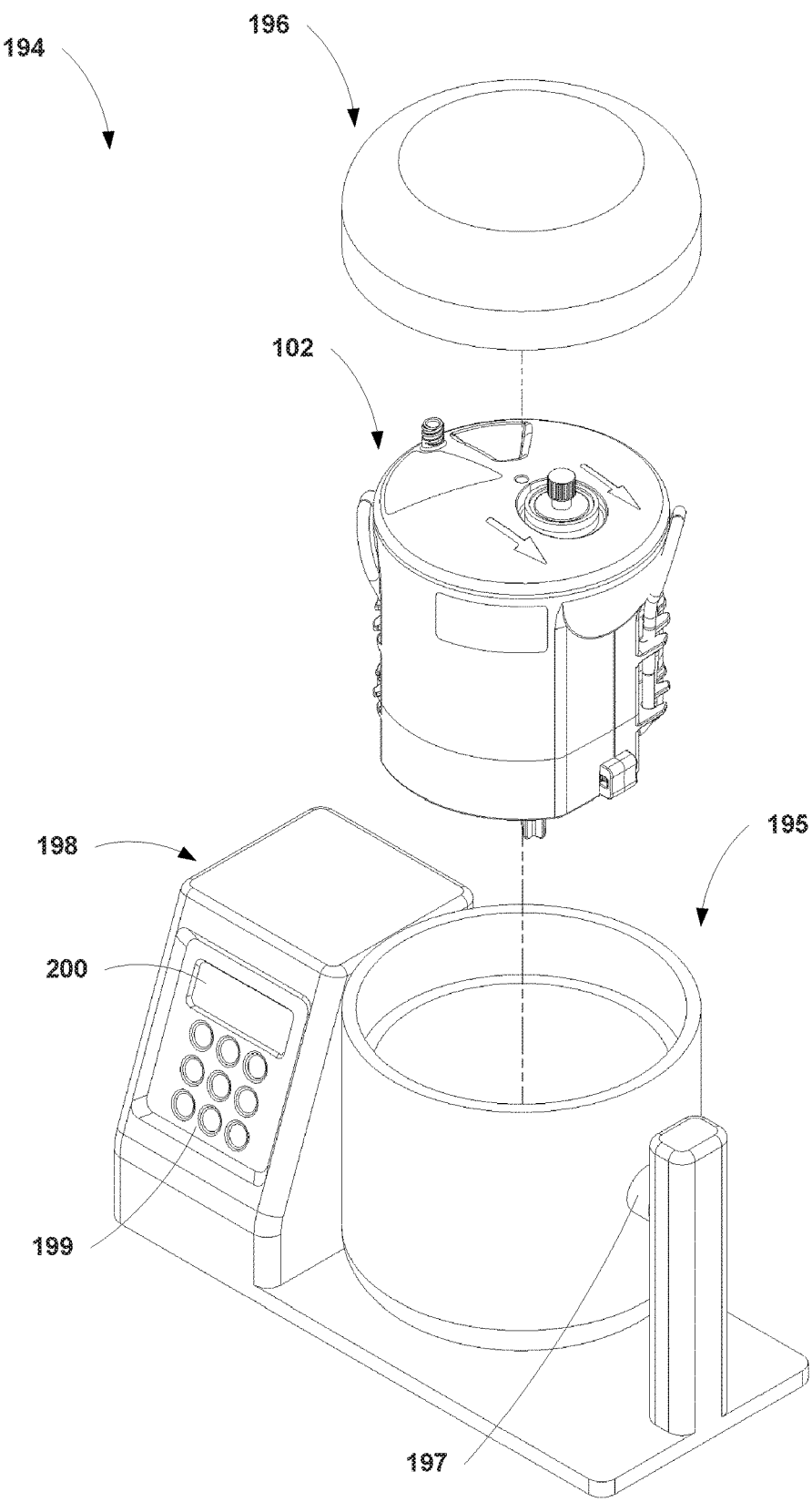
FIG. 8 is an exploded view of an example mixing module, according to an example embodiment.

In yet another non-limiting embodiment, as shown in FIG. 8, the mixer comprises a mixing module 194. The mixing module may include a bottom portion 195 and a top portion 196. As shown in FIG. 8, the cartridge 102 may be configured to be positioned in the bottom portion 195, and the top portion 196 may be configured to be removably coupled to the bottom portion 195. As such, the cartridge 102 may be positioned in a chamber created by the bottom portion 195 and the top portion 196. In one non-limiting embodiment, the mixing module 194 may include a rotatable component 197 coupled to the bottom portion 195. The rotatable component 197 may be configured to rotate the cartridge 102 on its vertical axis. The rotatable component 197 may be coupled to a motor, which in turn causes the bottom portion 195 of the mixing module 194 to rotate. In one particular example, the rotatable component 197 is configured to rotate the cartridge 102 on its vertical axis by 180 degrees, so the bottom of the cartridge 102 is in a vertical position, and then the rotatable component 197 causes the cartridge 102 to rotate back 180 degrees to an original upright position. In another example, the rotatable component 197 is configured to rotate the cartridge 102 end over end continuously over 360 degrees at various rotational rates for a period of time. In another non-limiting embodiment, the bottom portion 195 of the mixing module 194 may be configured to vibrate to assist in mixing. In another non-limiting embodiment, the mixing module 194 may be configured to increase a temperature of the cartridge 102 when the cartridge is positioned in the bottom portion 195 of the mixing module 194. Such an increase in temperature may occur through conduction, convection, or radiation heating in the bottom portion 195 of the mixing module 194.

As shown in FIG. 8, the mixing module 194 may include a mixing control module 198, which may include a control panel 199 and a display 200. The control panel 199 may be used to select a time period for mixing, as well as one or more mixing parameters. For example, a user could select 180 degree mixing for a period of time, 360 degree mixing for a period of time, heating at a specific temperature for a period of time, and/or vibrating for a period of time. Other examples are possible as well.

In various embodiments, the first medium input conduit 158 and/or the second medium input conduit further comprise a filter 186. Any suitable filter (including but not limited to a 0.2 micron filter, or other appropriately sized filter to remove large particles) can be used in connection with the medium input conduit(s) to promote aseptic introduction of medium into processing container and/or target container. Exemplary placement of such filters can be seen, for example, in FIG. 3.

In another embodiment, the second container 116 comprises an exit port 188 coupled to a first waste conduit 190. This embodiment permits removal of waste product from the second container 116. In a further embodiment, the processing container 108 further comprises a sterile vent 192 coupled to a second waste conduit (not shown). This embodiment permits removal of waste product from the processing container 108. Exemplary placement of such a sterile vent 192 can be seen, for example, in FIGS. 1 and 2.

In another embodiment, the methods further comprise administering to a subject in need thereof an amount of the harvested activated cell population or a harvested transduced cell population effective to treat a disorder in the subject. Genetic modification of human T cells is an increasingly important step in the development and manufacturing of therapeutic live cell-based therapies such as chimeric antigen receptor T (CAR-T) cells. CAR-T cells, such as the first-of-its-kind FDA-approved KYMRIAH (tisagenlecleucel) for acute lymphoblastic leukemia, are a patient's own (autologous) T lymphocytes manufactured into cancer-killing cells. Thus, in one embodiment the subject is suffering from cancer, including but not limited to lymphoblastic leukemia, hematologic cancers including leukemias and lymphomas, malignant melanoma, solid tumors, or metastatic cancers, and the methods comprise administering the harvested transduced cells to the subject to treat the cancer. Any suitable administrative route may be used, including but not limited to intravenous infusion. Any suitable dose of the harvested transduced cells may be used as deemed appropriate by attending medical personnel; in one embodiment, a therapeutic dose of CAR-T cells may be $0.2 \times 10^6$ to $2.5 \times 10^8$ viable CAR-expressing T cells CAR-T cell manufacturing is but one example of a process in which the methods of the disclosure may be efficient and advantageous. Other examples include different types of genetic engineering of autologous T- or B-cells now under development to treat diseases other than blood cancers, including ADA immunodeficiency, Wiskott-Aldrich syndrome immunodeficiency, tumors/melanoma, AIDS, autoimmune diseases, diabetes, hemophilia, uveitis, and encephalomyelitis.

In another aspect, isolated cell suspensions are provided, comprising a harvested activated cell population or a harvested transduced cell population produced by the methods of any embodiment or combination of embodiments disclosed herein. In one embodiment, the harvested transduced cell population comprises or consists of CAR-T cells. In a further aspect, methods are provided for treating a subject in need thereof, comprising administering to the subject an amount of isolated cell suspensions (such as CAR-T cells) effective to treat a disorder (including but not limited to cancer) in the subject.

In another aspect, the disclosure provides kits comprising any combination of:

(a) Microbubbles for the activation and transduction of a target cell type, wherein the kit provides either:
  (i) manufactured reagents, wherein the microbubbles and antibodies are provided already attached to each other, optionally via intermediate linkers, or
  (ii) separately packaged microbubbles and antibodies with complementary linkers, which spontaneously assemble into antibody bound microbubbles when added to the host liquid;
(b) one or more cartridges of the type disclosed in the '394 patent;
(c) buffers suitable for use with the provided reagents and cartridges to activate and transduce the target cells;
(d) buffers suitable for viral transduction of the activated target cells within the provided cartridges;
(e) viral vectors suitable for transduction of the activated target cells within the provided cartridges.

Example 1

Isolation and Activation of T Lymphocytes with a Microbubble/Buoyant Reagent

In order to compare the performance of CD3+ T cells isolated and activated by either the methods of the present disclosure or by conventional methods, the following protocol was used:

Cell Isolation and Activation with CD3/28 BACS Reagent:

1. A healthy human peripheral blood mononuclear cell (PBMC) preparation was prepared via centrifugation without Ficoll by processing fresh blood in the cartridge device of the '394 patent. Briefly, this involved:

a. One hundred and seventy mL of peripheral blood was placed in the cartridge's main chamber and 10 mL of Dulbecco's phosphate buffered saline plus 1% human serum albumin and 2 mM EDTA (DPBS-AE) was placed in the harvest chamber.

b. The blood was stratified by centrifugation at 2000×g for 20 minutes, depleted of erythrocytes at 50×g for 5 minutes, re-stratified at 1000×g for 5 minutes, and depleted of remaining erythrocytes at 50×g for 1 minute. Then the cells remaining in the main chamber were re-suspended by gentle hand mixing, the mononuclear cells (MNCs) were sedimented at 1000×g for 1 minute and then transferred to the harvest chamber at 50×g for 2 minutes, yielding a total MNC suspension volume of 13 mL.

2. An aliquot of the resulting PBMC preparation was enumerated using a hematology analyzer and the remaining MNCs were diluted to $30 \times 10^6$ MNCs per mL in DPBS-AE.

3. Two 2 mL aliquots of the diluted PBMCs were transferred to 5 mL conical base tubes.

4. CD3+ T cells were isolated from the PBMC sample via buoyancy-activated cell sorting by the general method outlined in the '111 patent, specifically:

a. To each tube was added 5 ug of biotinylated anti-CD3 antibody (clone OKT3) and 20 ug biotinylated anti-CD28 antibody (clone CD28.2).

b. The cell/antibody mixtures were incubated at room temperature for 20 minutes with gentle rocking.

c. $4 \times 10^8$ streptavidin-coated, gas-core, lipid-shell microbubbles of diameter >2 um (Bracco) were added to each tube and further incubated at room temperature with gentle rocking for an additional 20 minutes.

d. The tubes were centrifuged at 400×g for 5 minutes at room temperature to float the CD3+ cells and pellet all other cells.
e. The CD3+ floated cell/bubble rafts were transferred to 15 mL conical bottom tubes and adjusted to 3 mL total volume with DPBS-AE, resuspended, and immediately subjected to elevated pressure of approximately 2 atmospheres to irreversibly collapse the microbubbles (using a hand syringe to apply just sufficient gas pressure to clarify the milky bubble suspensions).

5. Cell activation proceeded by seeding the isolated CD3+ cells into T25 flasks at a density of $0.5 \times 10^6$ cells per mL in 6 mL of RPMI-1640 plus 10% fetal bovine serum (FBS), 30 U of IL-2 per mL, 100 IU/mL penicillin, and 100 ug/mL streptomycin and incubation for 24 h at 37° C. and 5% $CO_2$.

6. Following 24 h incubation, flow cytometric analysis was performed by staining cell aliquots with fluorescently labeled anti-CD25 and anti-CD69 antibodies or isotype controls.

7. Also following 24 h of incubation, $0.5 \times 10^6$ cells were seeded in 1 mL well plates and volume was increased to 1 mL with culture medium. Cells were expanded by incubation at 37° C. and 5% $CO_2$. The growing cells were split as necessary and cell counts were collected at intervals using a hematology analyzer.

Conventional Cell Isolation and Activation with CD3/28 Dynabeads:

1. From the same unit of fresh blood used for the BACS cell isolation (above), a PBMC prep was prepared, using Ficoll, involving:
a. 30 mL of blood was diluted to 60 mL with Dulbecco's phosphate buffered saline (DPBS)
b. To two 50 mL conical tubes was added 15 mL each of Ficoll-Paque Plus (GE Healthcare), and 30 mL of diluted blood was carefully layered atop the Ficoll in each tube. The tubes were then centrifuged at 400×g for 35 minutes with the brake off.
c. The upper plasma/platelet layers were carefully removed and discarded, and the MNC layers were carefully removed and combined in a single 50 mL conical tube and diluted to 45 mL with DPBS+0.5% human serum albumin (DPBS-A).
d. The MNC suspension was washed twice with DPBS-A (45 mL, 400×g for 10 minutes) and resuspended to a final volume of 5 mL in MACS buffer (DPBS-A+2 mM EDTA).

2. MNCs were enumerated in an aliquot of the MNC suspension using a hematology analyzer, and $50 \times 10^6$ MNCs were transferred to a 5 mL conical tube.

3. MNCs in MACS buffer were centrifuged at 300×g for 10 minutes, and the supernatant was removed and replaced with 4° C. MACS buffer to a final volume of 400 uL, to which was added 100 uL of Miltenyi Biotec anti-CD3 microbeads. The cell/bead suspension was then incubated at 4° C. for 15 minutes.

4. Seven mL of 4° C. MACS buffer was added, the tube was centrifuged at 300×g for 10 minutes, the supernatant was removed completely, and the cells/beads were resuspended in 500 uL of 4° C. MACS buffer.

5. An LS column in a midi-MACS magnet (Miltenyi Biotec) was prepared by rinsing the column with 3 mL of MACS buffer. The cell/bead suspension was pipetted onto the column, followed by 3×3 mL of MACS buffer.

6. The column was removed from the magnet and the positive cell fraction was collected by flushing it with 5 mL MACS buffer, finishing with a column plunger.

7. $3 \times 10^6$ isolated CD3+ cells were added to each of 2 T25 flasks.

8. 250 uL of CD3/CD28 Human T-Activator Dynabeads were placed in a 15 mL conical tube, to which 750 uL of MACS buffer was added. The tube was then placed on a Dynamag device. After 1 minute the supernatant was removed completely, 250 uL of MACS buffer was added, the tube was removed from the Dynamag, and the bead suspension was thoroughly mixed.

9. 75 uL of the bead suspension was added to each T25 flask of cells and thoroughly mixed (approximately 1 Dynabead per cell).

10. The cell suspension volumes were increased to 6 mL each with culture medium (RPMI-1640 plus 10% fetal bovine serum (FBS), 30 U of IL-2 per mL, 100 IU/mL penicillin, and 100 ug/mL streptomycin) and the flasks were incubated for 24 h at 37° C., 5% $CO_2$. After 24 h 0.5 mL was removed for cell analysis (flow cytometry with fluorescently labeled anti-CD69 and anti-CD25 antibodies).

11. Also following 24 h of incubation, $0.5 \times 10^6$ cells were seeded in 1 mL well plates and volume was increased to 1 mL with culture medium. Cells were expanded by incubation at 37° C. and 5% $CO_2$. The growing cells were split as necessary and cell counts were collected at intervals using a hematology analyzer.

12. Dynabeads were removed from cells prior to cell analysis by suspending bead/cell aliquots in 0.5 mL DPBS, thoroughly mixing, and separating the beads from cells on the Dynamag.

Figure 9:
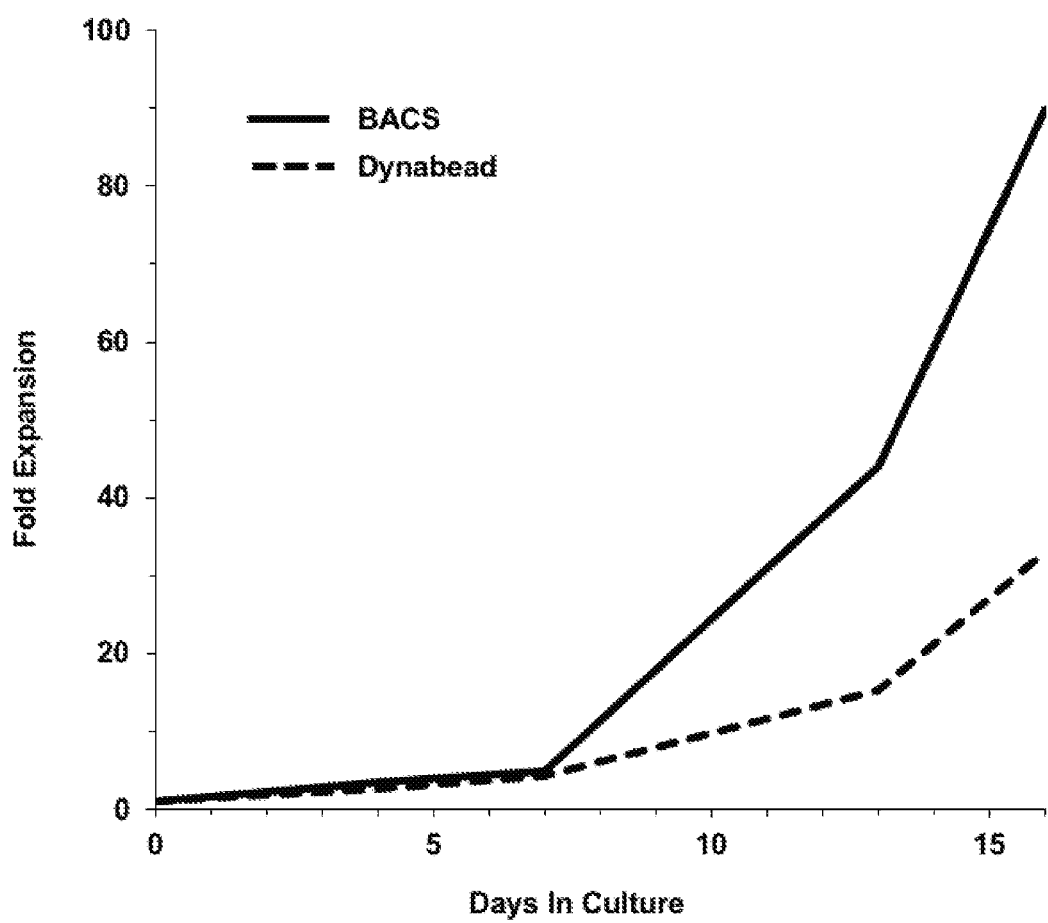
FIG. 9: Growth curves of CD3+ T cells activated with either CD3/CD28 BACS microbubbles or with CD3/CD28 Dynabeads™.

Results:

Cell expansion is a particularly relevant measure of naïve T cell activation in the context of therapeutic cell manufacturing because the low number of patient-derived starting cells must be substantially expanded to provide a therapeutic dose. FIG. 9 illustrates the growth curves over 16 days in culture for the CD3+ T cells activated by the method of the present disclosure with CD3/CD28 microbubbles (solid line) or by conventional means with CD3/CD28 Dynabeads (dashed line). In this experiment BACS-mediated expansion greatly exceeded that mediated by Dynabeads, achieving 90-fold expansion versus 33-fold, respectively. This is a surprising result because both common practice and the manufacturer's instructions dictate that Dynabeads should remain in contact with the cells for 1 to 3 days for efficient activation, whereas the labile microbubbles used here were collapsed by application of pressure immediately after cell isolation and are no longer observable on the cells by the time they enter culture at 37° C. Without being bound by any mechanism, the inventors speculate that labile BACS microbubbles' ability to efficiently activate cell expansion may derive from the collapsed bubbles' lipid shells with their bound antibodies remaining in intimate contact with the isolated cells' surfaces for an extended period of time in culture.

The experiment of this Example also reveals that microbubbles are efficient activators by the alternative measure of cell surface immunophenotype, specifically the activation-induced surface expression of the markers CD69 (considered an early marker of activation) and CD25 (considered a later marker). 77% of BACS-activated cells expressed CD69 versus 91% for Dynabead-activated cells, and 66% of BACS-activated cells expressed CD25 versus 88% of Dynabead-activated cells.

Example 2

Microbubbles Themselves do not Activate T Cells Non-Specifically

To test whether activation of T cells by BACS reagents might be molecularly non-specific (that is, a function of the lipid-shell gas-core microbubbles themselves, irrespective of the antibodies binding them to T cells), we compared T cell isolation/activation using anti-CD3/CD28 microbubbles to that using anti-CD4/CD8 microbubbles. CD4 and CD8 are T cell surface antigens that are not involved in triggering T cell activation.

Healthy human T cells (from a donor different from that of Example 1) were isolated, activated, and expanded with BACS reagents as detailed in Example 1, performing the isolation/activation steps with either anti-CD3/CD28 antibody-associated microbubbles or with anti-CD4/anti-CD8 antibody-associated microbubbles. After 14 days in culture the T cells isolated with CD3/CD28 microbubbles had expanded 2,247-fold, while T cells from the same donor isolated with CD4/CD8 microbubbles had expanded by only 7-fold (FIG. 2), demonstrating that only the former cells were substantially activated by their BACS reagent. Similarly, post-activation the cells isolated with anti-CD4/CD8 showed very low levels of CD69 and CD25 expression (3% and 8% of cells, respectively), whereas 87% and 71% of cells isolated with anti-CD3/CD28 were CD69+ and CD25+, respectively. Thus, microbubbles themselves do not activate T cells.

Figure 10:
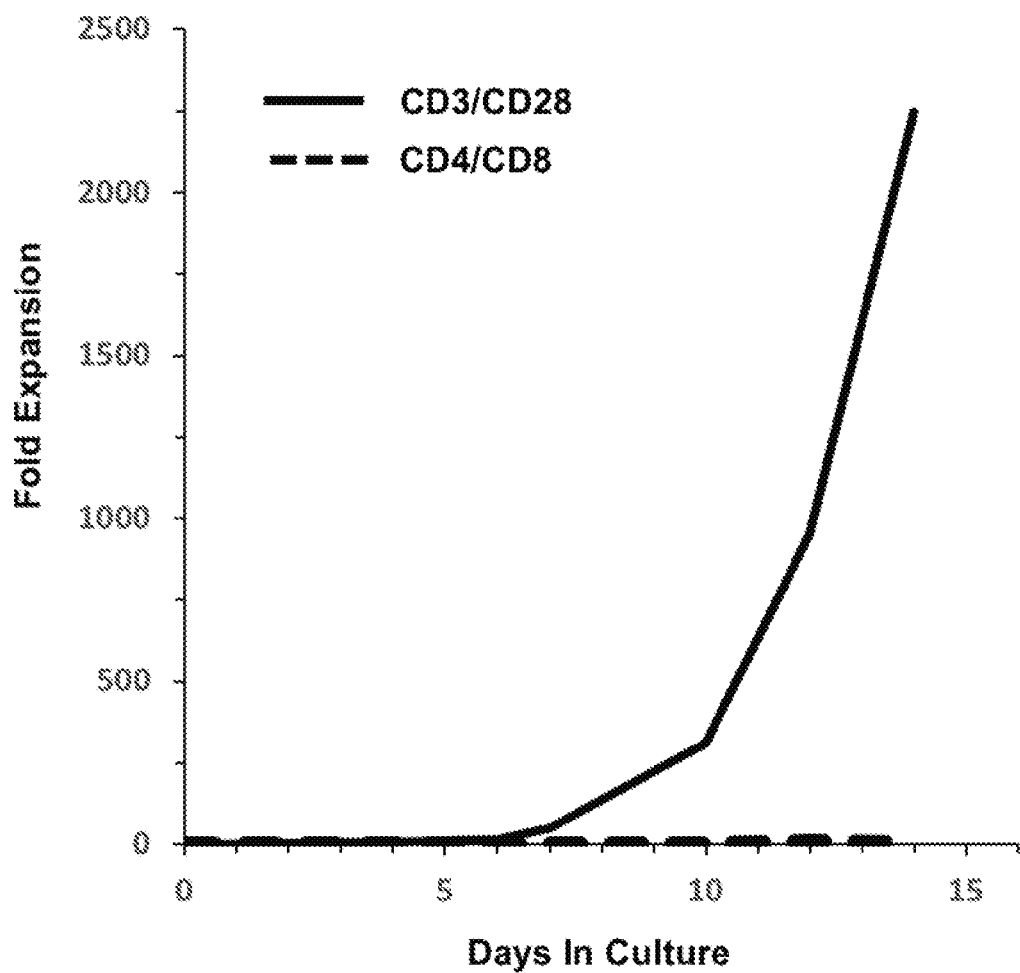
FIG. 10: Growth curves of T cells isolated and activated with either CD3/CD28 BACS microbubbles or with CD4/CD8 BACS bubbles.

In a control arm of this experiment (not shown in FIG. 10) in which T cells were isolated with anti-CD4/CD8 Dynabeads and then contacted with anti-CD3/CD28 microbubbles after removal of the Dynabeads, the cells expanded 1,625-fold after the same incubation period, demonstrating that CD4+ CD8+ T cells include T cells that are activation-competent with respect to CD3/CD28 BACS reagent.

Example 3

Viral Transduction of T Lymphocytes Activated with a Microbubble/Buoyant Reagent The purpose of activating CD3+ T cells for the production of CAR-T cells is to render the T cells susceptible to viral transduction with the synthetic chimeric antigen receptor gene. In this Example, CD3+ T cells isolated and activated by the methods outlined in Example 1 were therefore transduced with viral vector—in this case bearing the gene for green fluorescent protein (GFP)—to confirm that BACS-activated cells can be transduced similarly to conventional Dynabead-activated cells.

1. Healthy human CD3+ T cells (from a donor different from those of Examples 1 and 2) were isolated and activated either with CD3/CD28 BACS microbubbles or with CD3/CD28 Dynabeads as described in Example 1. After 36 hours of incubation in T25 flasks at 37° C. and 5% $CO_2$ the activated cells were seeded at $0.5 \times 10^6$ cells per mL into 1 mL wells coated with Retronectin (10 ug/cm$^2$).

2. Lentiviral vector pMNDU3-LUC-PGK-EGFP-WPRE (produced in HEK 293T cells), bearing a GFP transgene, was added to each well at a multiplicity of infection (MOI) of 5.

3. Virus/cell suspensions were incubated at 37° C. and 5% $CO_2$ for 48 h.

4. Following the 48 h incubation the cells were harvested, free virus was washed off 2× with fresh culture medium, and the cells were seeded into 1 mL wells at $0.5 \times 10^6$ per mL for expansion studies as described in Example 1.

5. Approximately 96 h following addition of virus, aliquots of cells were analyzed via flow cytometry for GFP fluorescence (cells gated on forward and side scatter).

Results:

At 96 h post virus addition, 48% of cells that were conventionally isolated/activated with magnetic CD3 microbeads and CD3/CD28 Dynabeads were found to express GFP, similar to the 47% of cells isolated/transduced via CD3/CD28 BACS microbubbles that expressed GFP. This result confirms that BACS-treated cells are as fully activated (and thus susceptible to lentiviral transduction) as are Dynabead-activated cells.

With this donor, Dynabead-treated cells displayed a level of expansion more nearly comparable to BACS-treated cells (116-fold versus 124-fold, respectively, through 7 days of expansion) than did the donor cells of Example 1, but Dynabead-activated cell expansion still did not exceed BACS microbubble-activated expansion. Similarly, cell activation as measured by CD69 and CD25 expression were nearly equivalent between the two activation methods, as reported in FIG. 11. Cell viability of transduced cells, as measured by 7-AAD exclusion via flow cytometry, was also nearly equivalent (96% for BACS-activated cells, 93% for Dynabead-activated cells).

These results further underscore the surprising nature of the present disclosure: namely that only brief contact (approximately 1-2 h) with intact gas-filled CD3/CD28 microbubbles achieves transduction-competent T cell activation equaling or exceeding that of CD3/CD28 Dynabead activation typically requiring 1 to 3 days of cell/bead contact.

Example 4

'One-Pot' Target Cell Isolation, Activation, Transduction and Incubation

In order to demonstrate the feasibility and practicality of the one-pot cell manufacturing process of the present invention, CD3+ T cells were isolated, activated, transduced and further incubated in a single cartridge device of the '394 patent, while the cartridge remained a functionally-closed system. Briefly, this involved:

1. A healthy human peripheral blood mononuclear cell (PBMC) preparation was prepared from whole blood (from a donor different from those of Examples 1 through 3) essentially via the method of Example 1, steps 1-2. All subsequent steps listed below (excepting only the analysis of cell aliquots) were performed in the single cartridge device of the '394 patent.

2. CD3+ T cells were isolated from the host liquid and activated as follows:

a. To the 15 mL suspension of PBMCs in DPBS-AE in the cartridge's processing container was added anti-CD3 and anti-CD28 biotinylated antibodies at a 2-to-1 ratio and incubated with gentle rocking for 30 minutes.

b. To the cell/antibody suspension in the cartridge was next added 6 mL of streptavidin-coated microbubbles (Bracco) containing $1.4 \times 10^8$ microbubbles per mL>2 um diameter. The cell suspension was then brought up to 80 mL by addition of DPBS-AE, and the resulting suspension within the cartridge was incubated for 20 minutes with gentle rocking.

c. The cartridge was centrifuged at 400×g for 5 minutes to pellet the negative fraction (non-microbubble-bound cells devoid of CD3), which was removed to the cartridge's waste compartment under the cartridge controller's programmatic control, leaving a 40 mL suspension of the positive fraction (target cells).

d. The positive fraction (floating CD3+ T cells bound to microbubbles) isolated in the cartridge's processing container was freed of intact microbubbles by brief application of approximately 3 atmospheres air pressure, permanently collapsing and/or disrupting the microbubbles. The target cells were then resuspended in the main compartment by adding RPMI1640+10% fetal bovine serum+30 IU IL-2 to a final volume of 120 mL.

3. Target cells were allowed to fully activate by incubating the cells, still in the cartridge's processing container, at 37° C. for 44 hours. During incubation, the headspace atmosphere of the processing container was refreshed every 2 hours by brief gentle streaming of 5% $CO_2$ in air into the headspace, through one of the cartridge's 0.2 um filters. Aliquots of cells for analysis were removed at 20 and 44 hours.

4. Target cells were then washed once by pelleting them at the bottom of the cartridge's main compartment, removing supernatant via the cartridge's central tube, and resuspending the target cells by adding fresh medium to the cartridge to a final concentration of about $1 \times 10^6$ cells per mL.

5. Cells were transduced within the cartridge by adding the lentiviral vector described in Example 3, step 2, at a MOI of 5, to the cell suspension in the main compartment.

6. Cells were allowed to transduce by incubating the cell/lentivirus suspension (still in the cartridge) for 48 hours at 37° C., briefly purging the headspace every 4 hours as described in Step 4 above, with gentle mixing.

Results:

One-pot isolation, activation and transduction of CD3+ T cells in a single, functionally closed cartridge device proved both feasible and successful in this pilot study. Immediately following CD3+ T cell isolation within the cartridge using anti-CD3/anti-CD28-linked microbubbles, followed by disruption of the microbubbles, baseline expression of activation markers was low but already detectable via flow cytometry (8.4% CD25+ cells; 0.0% CD69+). By 20 hours post-isolation CD25 expression had reached 39.2%, with CD25 expression reaching 35.7%. By the end of the allotted 44-hour activation period, CD25 expression was falling (27.4% CD25+) while CD69 expression had increased to 67.5% CD69+ cells.

Subsequent transduction of the activated cells, in the same cartridge, was also achieved, with 25.2% of transduced cells expressing detectable GFP fluorescence at 48 hours following adenovirus addition. In a parallel control (cartridge+cells with no addition of adenoviral vector) 0% of cells expressed GFP fluorescence at this same timepoint.

The results of this experiment are surprising because they contradict the commonly expressed belief, reflected in published protocols for T cell transduction, that extended (multi-day) contact between cells and anti-CD3/anti-CD28 carrier microbodies (Dynabeads, vesicles, liposomes, etc.) is required for efficient activation of cells preceding and during lentiviral transduction. Under the conditions employed here, intact anti-CD3/anti-CD28 microbubbles were in contact with the target CD3+ T cells no longer than the approximately 30 minutes required to isolate the CD3+ cells and to collapse and/or disrupt the microbubbles by momentary application of elevated air pressure, yet productive transduction was nonetheless achieved. This lack of reliance upon multi-day contact renders one-pot isolation, activation and transduction of BACS-isolated cells feasible, because intact BACS microbubbles in the presence of cells and culture medium at 37° C. have lifetimes of only a few hours, rather than days.

Example 5

Minimum Practical Contacting Time for BACS-Mediated Target Cell Isolation

Like most other physicochemical binding reactions, the temporal course of the binding reaction in which antibodies and microbubbles bind to target cells in a host liquid to an extent sufficient to achieve BACS-mediated target cell isolation is likely to be described by a roughly asymptotic curve, with a relatively high (but incomplete) percentage of target cells bound rapidly, followed by a slower completion of the binding reaction to approach 100% of target cells bound. In order to better define the practical minimum time interval required for contacting the host liquid containing target cells with the antibodies and microbubbles, the following experiment was performed, with all conditions listed below tested in duplicate:

1. 5 mL aliquots of healthy human undiluted blood were added to capped plastic 15 mL tubes. To each tube was next added 100 uL biotinylated anti-CD3 antibody solution at 0.025 ug/uL.

2. The tubes containing blood plus antibody were incubated for 10, 15, or 30 minutes at either room temperature or 4° C. with gentle rocking.

3. Immediately following the antibody incubation period, to each tube was added 600 uL of streptavidin-coated microbubble suspension (Bracco) containing $0.8 \times 10^8$ microbubbles >2 um diameter. Tubes were then quickly mixed by manual inversion and further incubated either 30 seconds or zero seconds.

4. The tubes were centrifuged at 400×g for 5 minutes to separate target CD3 cells from non-target cells. Positive (floating) cells and negative (pelleted) cells were separately collected by manual pipetting of the bubble raft at the liquid's meniscus, and CD3+ target cell recovery was determined by flow cytometry.

Results:

Average CD3+ target cell recovery as a function of antibody incubation time and temperature (N=2; RT=room temperature):

| Antibody incubation time (minutes) | % recovery at 4° C. incubation | % recovery at RT incubation |
|---|---|---|
| 10 | 49% | 51% |
| 15 | 50% | 61% |
| 30 | 50% | 76% |

(NB: 30-minute antibody incubation at RT without a subsequent 30-second microbubble incubation yielded a target cell recovery of 55%)

The results of this experiment support the hypothesis that substantial binding of effective antibody/microbubble complexes to target cells is initially rapid but incomplete, progressing roughly asymptotically toward completion with further incubation: at either 4° C. or RT about 50% of target cells were recovered with just a 10-minute antibody incubation followed by either 0-second or 30-second microbubble incubation, while with RT antibody incubation recovery further increased to 61% and 76% with 15 minute and 30 minute incubation, respectively. At 4° C. the asymptotic approach to completion was substantially slower.

We claim:

1. A method for isolation and activation of target cells, comprising
(a) contacting in a closed container a host liquid comprising the target cells with gas-core lipid-shelled microbubbles and one or more antibodies that bind to cell surface molecules on the target cells, wherein the one or more antibodies are bound to the target cells or the microbubbles, and wherein the contacting produces target cells linked to the microbubbles via the one or more antibodies;
(b) isolating in the closed container the target cells linked to microbubbles from the other cells in the host liquid to produce isolated target cells linked to microbubbles;
(c) collapsing and/or disrupting in the closed container the microbubble component of the isolated target cells linked to microbubbles between about 1 minute and about 180 minutes after initiating the contacting in step (a), wherein the collapsing and/or disrupting produces isolated target cells linked to microbubble residua; and
(d) culturing the isolated target cells linked to microbubble residua to produce activated target cells via the one or more antibodies linked to the microbubble residua.

2. The method of claim 1, comprising concentrating the isolated target cells linked to microbubbles in the closed container after step (b).

3. The method of claim 1, wherein the collapsing and/or disrupting the microbubble component of the isolated target cells linked to microbubbles occurs between about 2 minutes and about 60 minutes after initiating the contacting.

4. The method of claim 1, wherein the collapsing and/or disrupting the microbubble component of the isolated target cells linked to microbubbles occurs between about 5 minutes and about 30 minutes after initiating the contacting.

5. The method of claim 1, wherein the contacting comprises contacting in the host liquid (i) the target cells bound to the one or more antibodies with (ii) the microbubbles, wherein the microbubbles are capable of binding to the one or more antibodies directly or indirectly via a linker.

6. The method of claim 1, wherein the contacting comprises contacting in the host liquid (i) the target cells with (ii) the one or more antibodies bound to the microbubbles directly or indirectly via a linker.

7. The method of claim 1, wherein the method further comprises transducing the activated target cells, wherein the transducing comprises incubating the activated target cells with a viral vector encoding a transgene.

8. The method of claim 7, wherein the transducing is carried out in the closed container.

9. The method of claim 7, wherein the activated target cells are activated $CD3^+$ T-cells, and wherein the transgene encodes a chimeric antigen receptor (CAR) comprising an extracellular anti-CD19 single chain antibody fragment and an intracellular T cell signaling domain comprising the CD3-ζ stimulatory domain and the 4-1BB co-stimulatory domain.

10. The method of claim 7, wherein the interval between initiating the contacting and initiating the transducing is between about 12 hours and about 36 hours.

11. The method of claim 1, wherein the method further comprises expanding the activated target cells, wherein the expanding comprises culturing the activated target cells under conditions suitable to promote proliferation of the activated target cells.

12. The method of claim 11, wherein the expanding is carried out in the closed container.

13. The method of claim 1, wherein the target cells are CD3+ T cells, and wherein the one or more antibodies comprise anti-CD3 and anti-CD28 antibodies.

14. The method of claim 1, wherein the host liquid is blood, leukapheresis product, or diluted or processed versions thereof.

15. The method of claim 1, wherein the host liquid comprises a peripheral blood mononuclear cell (PBMC) preparation.

16. The method of claim 11, wherein the method further comprises harvesting the expanded activated target cells to produce a harvested activated cell population, wherein the harvesting is optionally carried out in the closed container.

17. The method of claim 16, further comprising washing the harvested activated cell population, wherein the washing is optionally carried out in the closed container.

18. The method of claim 16, further comprising transferring the harvested activated cell population to a medium suitable for infusion, wherein the transferring is optionally carried out in the closed container.

19. The method of claim 1, wherein the host liquid is partially depleted of non-target cells prior to the contacting step.

20. The method of claim 1, wherein the closed container comprises:
(a) a cartridge comprising
(i) a processing container comprising at least one input port, a first exit port, and a second exit port;
(ii) a second container comprising an input port;
(iii) a third container comprising an input port and a first exit port;
(iv) a first conduit connecting the first exit port of the processing container and the input port of the second container, wherein the first conduit comprises a first reversible closing device, wherein the second container is transiently fluidically connected to the processing container such that fluid flows from the processing container to the second container only when the first reversible closing device is opened;
(v) a second conduit connecting the second exit port of the processing container and the input port of the third container, wherein the second conduit comprises a second reversible closing device, wherein the third container is transiently fluidically connected to the processing container such that fluid flows from the processing container to the third container only when the second reversible closing device is opened;
(b) a transfer container comprising at least one port;
(c) at least one third conduit connecting
(i) the first exit port of the third container to the at least one port of the transfer container, and
(ii) the at least one port of the transfer container to the at least one input port of the processing container;
wherein the at least one third conduit comprises at least a third reversible closing device, such that (A) the third container is transiently fluidically connected to the transfer container, and (B) the transfer container is transiently fluidically connected to the processing container; wherein the at least one third conduit is configured such that only one of the following may be true
(I) fluids flow from the third container to the transfer container only when the at least third reversible closing device is opened; or (II) fluid flows from the transfer container to the processing container only when the at least third reversible closing device is opened; and (d) a control module configured to control activity in at least the first and second conduits of the cartridge.

21. The method of claim 7, wherein the transduced target cells are CAR-T cells.

22. The method of claim 7, wherein the method further comprises expanding the transduced target cells, wherein the expanding comprises culturing the transduced target cells under conditions suitable to promote proliferation of the transduced target cells.

23. The method of claim 22, wherein the expanding is carried out in the closed container.

24. The method of claim 16, further comprising transferring the harvested activated cell population to a cryopreservation medium, wherein the transferring is optionally carried out in the closed container.

\* \* \* \* \*